US010661037B2

(12) United States Patent
Nadeau et al.

(10) Patent No.: US 10,661,037 B2
(45) Date of Patent: May 26, 2020

(54) INDIRECT MEASUREMENT IN A TOTAL LIQUID VENTILATION SYSTEM

(71) Applicant: SOCPRA SCIENCES ET GENIE S.E.C., Sherbrooke (CA)

(72) Inventors: Mathieu Nadeau, Compton (CA); Philippe Micheau, Sherbrooke (CA); Raymond Robert, Chambly (CA); Herve Walti, Sherbrooke (CA); Olivier Avoine, Iie Bizard (CA); Jean-Paul Praud, Sherbrooke (CA)

(73) Assignee: SOCPRA SCIENCES ET GÉNIE S.E.C., Sherbrooke, Quebec (CA)

( * ) Notice: Subject to any disclaimer, the term of this patent is extended or adjusted under 35 U.S.C. 154(b) by 1093 days.

(21) Appl. No.: 15/023,290

(22) PCT Filed: Jun. 25, 2014

(86) PCT No.: PCT/CA2014/000521
§ 371 (c)(1),
(2) Date: Mar. 18, 2016

(87) PCT Pub. No.: WO2014/205548
PCT Pub. Date: Dec. 31, 2014

(65) Prior Publication Data
US 2016/0271348 A1 Sep. 22, 2016

Related U.S. Application Data

(60) Provisional application No. 61/838,896, filed on Jun. 25, 2013.

(51) Int. Cl.
*A61M 16/00* (2006.01)
*A61M 16/04* (2006.01)
(Continued)

(52) U.S. Cl.
CPC ......... *A61M 16/0054* (2013.01); *A61B 5/01* (2013.01); *A61B 5/08* (2013.01); *A61B 5/087* (2013.01);
(Continued)

(58) Field of Classification Search
CPC ........... A61M 16/0054; A61M 16/026; A61M 16/0003; A61M 16/0069; A61M 16/0816;
(Continued)

(56) References Cited

U.S. PATENT DOCUMENTS

| 5,335,650 A | 8/1994 | Shaffer et al. |
| 5,429,123 A * | 7/1995 | Shaffer ............... A61M 16/024 128/204.21 |

(Continued)

OTHER PUBLICATIONS

Philippe Micheau et al (2011). A Liquid Ventilator Prototype for Total Liquid Ventilation Preclinical Studies, Progress in Molecular and Environmental Bioengineering—From Analysis and Modeling to Technology Applications, InTech, pp. 323-344 (Year: 2011).*

(Continued)

*Primary Examiner* — Justine R Yu
*Assistant Examiner* — Matthew R Moon
(74) *Attorney, Agent, or Firm* — Leason Ellis LLP

(57) ABSTRACT

A method, connector and system for obtaining an indirect measurement of a parameter in a patient with a total liquid ventilation (TLV) system. At least one parameter measurement is obtained of a liquid taken in the TLV system comprising an endotracheal tube having a distal end inserted in a patient's trachea. At least one flow measurement is obtained of a liquid taken in the TLV system. Considering a fluid model of the TLV system, the at least one parameter measurement and the least one flow measurement are processed into the indirect measurement of the parameter in the patient. The indirect measurement may be a temperature or pressure. The temperature can be a lung temperature, a blood (Continued)

temperature or an organ temperature. The pressure may be a tracheal pressure or an alveolar pressure.

34 Claims, 13 Drawing Sheets

(51) Int. Cl.
| | |
|---|---|
| *A61B 5/01* | (2006.01) |
| *A61B 5/087* | (2006.01) |
| *A61B 5/08* | (2006.01) |
| *A61M 16/08* | (2006.01) |
| *A61M 16/14* | (2006.01) |
| *A61M 16/10* | (2006.01) |
| *A61F 7/12* | (2006.01) |
| *A61F 7/00* | (2006.01) |

(52) U.S. Cl.
CPC .... *A61M 16/0003* (2014.02); *A61M 16/0069* (2014.02); *A61M 16/026* (2017.08); *A61M 16/04* (2013.01); *A61M 16/0816* (2013.01); *A61M 16/14* (2013.01); *A61F 7/0053* (2013.01); *A61F 7/12* (2013.01); *A61M 16/109* (2014.02); *A61M 2016/003* (2013.01); *A61M 2016/0018* (2013.01); *A61M 2016/0027* (2013.01); *A61M 2016/0036* (2013.01); *A61M 2205/3334* (2013.01); *A61M 2205/3368* (2013.01); *A61M 2205/3606* (2013.01); *A61M 2205/366* (2013.01); *A61M 2205/52* (2013.01); *A61M 2205/702* (2013.01); *A61M 2230/50* (2013.01)

(58) Field of Classification Search
CPC .. A61M 16/14; A61M 16/04; A61M 16/0463; A61M 2205/3368; A61M 2205/52; A61M 2205/3334; A61M 2205/366; A61M 2205/3606; A61M 2016/003; A61M 2016/0036; A61M 2016/0027; A61M 2016/0018; A61M 2205/702; A61M 16/109; A61M 2230/50; A61B 5/087; A61B 5/08; A61B 5/01; A61F 7/12; A61F 7/0053
See application file for complete search history.

(56) References Cited

U.S. PATENT DOCUMENTS

| | | | | | |
|---|---|---|---|---|---|
| 5,437,272 | A | * | 8/1995 | Fuhrman | A61M 16/0054 128/203.12 |
| 5,540,220 | A | * | 7/1996 | Gropper | A61M 16/024 128/204.21 |
| 5,540,225 | A | * | 7/1996 | Schutt | A61K 9/0026 128/207.15 |
| 5,622,182 | A | * | 4/1997 | Jaffe | A61B 5/01 600/531 |
| 5,706,830 | A | | 1/1998 | Parker | |
| RE36,460 | E | * | 12/1999 | Klatz | A01N 1/02 128/201.21 |
| 6,041,777 | A | | 3/2000 | Faithfull et al. | |
| 6,315,739 | B1 | * | 11/2001 | Merilainen | A61M 16/044 600/587 |
| 6,694,977 | B1 | * | 2/2004 | Federowicz | A61F 7/12 128/201.13 |
| 7,110,558 | B1 | * | 9/2006 | Elliott | H03G 3/32 381/104 |
| 7,909,031 | B2 | * | 3/2011 | Shaffer | A61M 16/0054 128/200.14 |
| 8,225,796 | B2 | * | 7/2012 | Davenport | A61B 5/087 128/207.18 |
| 8,312,879 | B2 | * | 11/2012 | Choncholas | A61M 16/12 128/204.23 |
| 2002/0153010 | A1 | * | 10/2002 | Rozenberg | A61M 16/0054 128/203.12 |
| 2003/0060764 | A1 | * | 3/2003 | Dua | A61M 1/008 604/129 |
| 2004/0122353 | A1 | * | 6/2004 | Shahmirian | A61M 5/14276 604/65 |
| 2005/0108057 | A1 | * | 5/2005 | Cohen | G16H 40/20 705/3 |
| 2008/0190426 | A1 | * | 8/2008 | Koch | A61M 16/16 128/203.16 |
| 2010/0012122 | A1 | * | 1/2010 | Shaffer | A61M 16/0054 128/204.18 |
| 2012/0024286 | A1 | * | 2/2012 | Boring | A61M 16/0051 128/204.21 |

OTHER PUBLICATIONS

Robert et al (2007). A supervisor for volume-controlled tidal liquid ventilator using independent piston pumps, Biomedical Signal Processing and Control, vol. 2 Issue 3, pp. 267-274 (Year: 2007).*
Robert et al (2009). Regulator for Pressure-Controlled Total-Liquid Ventilation, IEEE Transactions on Biomedical Engineering, vol. 57 issue 9, pp. 2267-2276 (Year: 2009).*

* cited by examiner

INDIRECT MEASUREMENT IN A TOTAL LIQUID VENTILATION SYSTEM

CROSS REFERENCE TO RELATED APPLICATIONS

The present application is a U.S. National Phase of International Patent Application PCT/CA2014/000521, filed Jun. 25, 2014, which claims priority to U.S. Patent Application 61/838,896, filed Jun. 25, 2013, all of which are incorporated herein by reference in their entirety.

TECHNICAL FIELD

The present invention relates to the field of artificial ventilators and, more particularly, to airway pressure and lung temperature.

BACKGROUND

Artificial mechanical ventilation concepts include mechanical ventilators, high frequency ventilators, and extracorporeal membrane oxygenation (ECMO) ventilators. Total liquid ventilation (TLV) is a radical departure from these concepts. With TLV, lungs of a patient are completely filled with liquid, for example perfluorocarbon (PFC), and a fluid ventilator provides a cyclic respiratory volume renewal.

Unfortunately, the deployment and use of the TLV technology in a clinical setting has been limited. The present invention aims at providing at least partial solutions to problems that are seen as limiting such deployment and use.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A first aspect of the present invention is directed to a method for determining an indirect measurement of a parameter in a patient with a total liquid ventilation (TLV) system. The method comprises a) obtaining at least one parameter measurement of a liquid taken in the TLV system comprising a tube having a distal end inserted in a patient's respiratory tract (e.g., an endotracheal tube inserted in a patient's trachea), b) obtaining at least one flow measurement of a liquid taken in the TLV system and c) processing, considering a fluid model of the TLV system, the at least one parameter measurement and the least one flow measurement into the indirect measurement of the parameter in the patient.

Optionally, obtaining the at least one parameter measurement may comprises obtaining at least one pressure measurement of the liquid taken in the TLV and processing the at least one measurement and the least one flow measurement into the indirect measurement of the parameter in the lung may then further comprise processing the at least one pressure measurement into a pressure drop value within the TLV system considering the fluid model of the TLV system and processing the at least one pressure measurement and the pressure drop value into the indirect measurement of the parameter in the patient's lung.

Steps a) to c) may be repeated periodically and/or may be performed in real-time.

Optionally, obtaining at least one measurement may be performed by receiving data in a plurality of data packets over a network interface.

The method may further comprise periodically storing at least the indirect airway pressure value and optionally the pressure measurement, the flow measurement and the pressure drop value into memory.

The method may further comprise obtaining a variation of the flow of the liquid. Processing the flow measurement into a pressure drop value within the endotracheal tube may then be performed further considering the variation of the flow of the liquid. Obtaining the variation of the flow of the liquid may also be performed by receiving data in a plurality of data packets over a network interface.

The method may also further comprise reading the fluid model of the TLV system from memory.

The method may also optionally further comprise determining and/or updating the fluid model of TLV system by determining a resistance of the endotracheal tube and an inertance of the liquid in the endotracheal tube.

The method may also further comprise controlling a pump of the TLV system based at least on the indirect airway pressure value.

Optionally, obtaining the at least one parameter measurement may comprise obtaining at least one temperature measurement of a liquid expelled from the lung via the tube. The fluid model of the TLV system may then be a thermodynamic model of the TLV system to estimate the thermal time constant in the TLV system based on flow value. Obtaining the temperature measurement of the liquid may be performed following a pause after an expiratory cycle of the patient.

Processing the at least one parameter measurement and the least one flow measurement into the indirect measurement of the parameter in the patient may further comprise processing more than one of the at least one flow measurement into flow rate integration to determine a time delay caused by thermal dead volume and processing the at least one temperature measurement considering the time delay the thermal time constant from the TLV model based on the at least one flow measurement.

The indirect measurement of the parameter in the patient may indicate temperature of the patient's lung, of the patient's blood and/or of another of the patient's organ. The temperature of the liquid may be measured at a junction of the tube (e.g., endotracheal) to expiratory and inspiratory circuits of the TLV system.

The method may further comprise controlling a treatment unit of the TLV system based at least on the indirect temperature measurement.

A second aspect of the present invention is directed to an analyzer for determining an indirect measurement of a parameter in a patient with a total liquid ventilation (TLV) system. The analyzer comprises a measurement interface module for a) obtaining at least one parameter measurement of a liquid taken in the TLV system comprising a tube having a distal end inserted in a patient's respiratory tract (e.g., an endotracheal tube inserted in a patient's trachea) and b) obtaining at least one flow measurement of a liquid taken in the TLV system. The analyzer also comprises a processor module for c) considering a fluid model of the TLV system, processing the at least one parameter measurement and the least one flow measurement into the indirect measurement of the parameter in the patient.

Optionally, the measurement interface module may obtain at least one parameter measurement by obtaining at least one pressure measurement of the liquid taken in the TLV. The processor module may then, when processing the at least one measurement and the least one flow measurement into the indirect measurement of the parameter in the lung, further process the at least one pressure measurement into a pressure drop value within the TLV system considering the fluid model of the TLV system and process the at least one pressure measurement and the pressure drop value into the indirect measurement of the parameter in the patient's lung.

a), b) and c) may be periodically repeated and/or performed in real-time.

The measurement interface may be a network interface and obtaining at least one measurement may thus further comprise receiving data in a plurality of data packets thereover.

The analyzer may further comprise a memory module for periodically storing at least the indirect airway pressure value and optionally the pressure measurement, the flow measurement and the pressure drop value thereinto.

The measurement interface may further obtain a variation of the flow of the liquid and the processor module may then further process the flow measurement into a pressure drop value within the tube considering the variation of the flow of the liquid. The measurement interface may be a network interface and obtaining the variation of the flow of the liquid may further comprise receiving data in a plurality of data packets thereover.

The analyzer may further comprise a table, stored in a memory module, comprising the fluid model of the TLV system.

The processor module may further determine and/or update the fluid model of TLV system by determining a resistance of the tube and an inertance of the liquid in the tube.

The analyzer may further comprise a pump controller module for controlling a pump of the TLV system based at least on the indirect airway pressure value.

Optionally, the measurement interface module may obtain the at least one parameter measurement by obtaining at least one temperature measurement of a liquid expelled from the lung via the endotracheal tube and wherein the fluid model of the TLV system is a thermodynamic model of the TLV system to estimate the thermal time constant in the TLV system based on flow value.

The measurement interface module may obtain the temperature measurement of the liquid following a pause after an expiratory cycle of the patient.

The processor module, when processing the at least one parameter measurement and the least one flow measurement into the indirect measurement of the parameter in the patient, may further process more than one of the at least one flow measurement into flow rate integration to determine a time delay caused by thermal dead volume and process the at least one temperature measurement considering the time delay the thermal time constant from the TLV model based on the at least one flow measurement.

The indirect measurement of the parameter in the patient may indicate temperature of the patient's lung, of the patient's blood and/or of another of the patient's organ. The temperature of the liquid may be measured at a junction of the tube to expiratory and inspiratory circuits of the TLV system.

The analyzer may further comprise a temperature controller module for controlling a treatment unit of the TLV system based at least on the indirect temperature measurement.

A third aspect of the present invention is directed to a method for determining an indirect measurement of a temperature parameter and an indirect measurement of a pressure parameter in a patient with a total liquid ventilation (TLV) system. The method comprises a) obtaining at least one pressure parameter measurement and at least one temperature parameter measurement of a liquid taken in the TLV system comprising a tube having a distal end inserted in a patient's respiratory tract, b) obtaining at least one flow measurement of a liquid taken in the TLV system; and c) considering at least one fluid model of the TLV system, processing the at least one pressure parameter measurement, the at least one temperature parameter measurement and the least one flow measurement into the indirect measurement of the indirect measurement of the temperature parameter and the indirect measurement of the pressure parameter.

The method may further comprise controlling a treatment unit of the TLV system based at least on the indirect temperature measurement and/or controlling a pump of the TLV system based at least on the indirect pressure measurement.

A fourth aspect of the present invention is directed to an analyzer for determining an indirect measurement of a temperature parameter and an indirect measurement of a pressure parameter in a patient with a total liquid ventilation (TLV) system. the analyzer comprises a measurement interface module and a processor module. The measurement interface module is for a) obtaining at least one pressure parameter measurement and at least one temperature parameter measurement of a liquid taken in the TLV system comprising a tube having a distal end inserted in a patient's respiratory tract and b) obtaining at least one flow measurement of a liquid taken in the TLV system. The processor module is for c), considering at least one fluid model of the TLV system, processing the at least one pressure parameter measurement, the at least one temperature parameter measurement and the least one flow measurement into the indirect measurement of the indirect measurement of the temperature parameter and the indirect measurement of the pressure parameter.

The analyzer may further comprise a temperature controller module for controlling a treatment unit of the TLV system based at least on the indirect temperature measurement and/or a pump controller module for controlling a pump of the TLV system based at least on the indirect pressure measurement.

Another aspect of the present invention may relate to a connector, comprising a junction for connecting expiratory and inspiratory circuits of a total liquid ventilation (TLV) system to a proximal end of an endotracheal tube having a distal end insertable in a patient's trachea, a pressure sensor, located within the junction, for measuring a pressure of a liquid present in the endotracheal tube and an interface for outputting pressure measurements of the liquid. The connector may comprise a flow sensor, located within the junction, for measuring a flow of the liquid within the endotracheal tube.

Another aspect of the present invention may relate to a TLV system configured to receive pressure and flow measurements of the liquid from the above connector, the TLV system comprising an analyzer configured to estimate a pressure drop within the endotracheal tube as a function of the flow of the liquid and as a function of a fluid model of the endotracheal tube and calculate an indirect airway pressure of the patient as a function of the measured pressure at the proximal end of the endotracheal tube and as a function of the estimated pressure drop within the endotracheal tube.

Another aspect of the present invention may relate to a TLV system configured to receive pressure measurements of the liquid from the above connector, the TLV system comprising a flow sensor, for measuring a flow of the liquid entering or leaving the endotracheal tube and an analyzer configured to estimate a pressure drop within the endotracheal tube as a function of the flow of the liquid and as a function of a fluid model of the endotracheal tube and calculate an indirect airway pressure of the patient as a function of the measured pressure at the proximal end of the endotracheal tube and as a function of the estimated pressure drop within the endotracheal tube.

Another aspect of the present invention may relate to a connector, comprising a junction for connecting expiratory and inspiratory circuits of a total liquid ventilation (TLV) system to a proximal end of an endotracheal tube having a distal end insertable in a patient's trachea, a temperature sensor, located within the junction, for measuring a temperature of a liquid expelled from the patient's lungs via the endotracheal tube and an interface for outputting temperature measurements of the liquid.

Another aspect of the present invention may relate to a TLV system configured to receive temperature measurements of the liquid from the above connector, the TLV system comprising an analyzer configured to detect the end of an expiratory cycle and determine an indirect lung temperature by selecting a temperature measurement of the liquid received upon detection of the end of the expiratory cycle.

Another aspect of the present invention may relate to a TLV system configured to receive temperature measurements of the liquid from the above connector, the TLV system comprising an analyzer configured to detect the end of a dead volume retrieved from the lung, detect the end of an expiratory cycle and determine a lung temperature based on measurements of the liquid temperature obtained between the end of the dead volume and the end of the expiratory cycle.

Another aspect of the present invention may relate to an indirect airway pressure measurement method for use with a total liquid ventilation (TLV) system, comprising measuring a pressure of a liquid in the TLV system comprising an endotracheal tube having a distal end inserted in a patient's trachea, measuring a flow of the liquid within the TLV system, estimating a pressure drop within the TLV system as a function of the flow of the liquid and as a function of a fluid model of the endotracheal tube and calculating an indirect airway pressure of the patient as a function of the measured pressure and as a function of the estimated pressure drop. Measuring the pressure of the liquid may be performed at a proximal end of the endotracheal tube and the flow of the liquid is measured in the endotracheal tube. The pressure drop within the endotracheal tube may be estimated as a function of the flow of the liquid and as a function of a variation of the flow of the liquid. The method may further comprise determining the fluid model of the endotracheal tube by determining a resistance of the endotracheal tube and an inertance of the liquid in the endotracheal tube. A resistance value for the lung may be used in estimating the pressure drop, the indirect airway pressure being indicative of alveolar pressure within the lung.

Another aspect of the present invention may relate to use of the indirect airway pressure measurement obtained using the above method for controlling a pump of the TLV system.

Another aspect of the present invention may relate to an indirect lung temperature measurement method for use with a total liquid ventilation (TLV) system, comprising, measuring a temperature of a liquid expelled from the patient's lungs via an endotracheal tube having an end inserted in a patient's trachea. The temperature of the liquid at the proximal end of an endotracheal tube may be obtained during a pause following the expiratory cycle of the patient. The temperature of the liquid may be measured at a junction of the endotracheal tube to expiratory and inspiratory circuits of the TLV system.

Another aspect of the present invention may relate to use of the indirect lung temperature measurement obtained using the above method for controlling a body temperature or an arterial blood temperature of the patient and/or for controlling a temperature of the liquid.

BRIEF DESCRIPTION OF THE DRAWINGS

Further features and exemplary advantages of the present invention will become apparent from the following detailed description, taken in conjunction with the appended drawings, in which.

DETAILED DESCRIPTION

Figure 1:
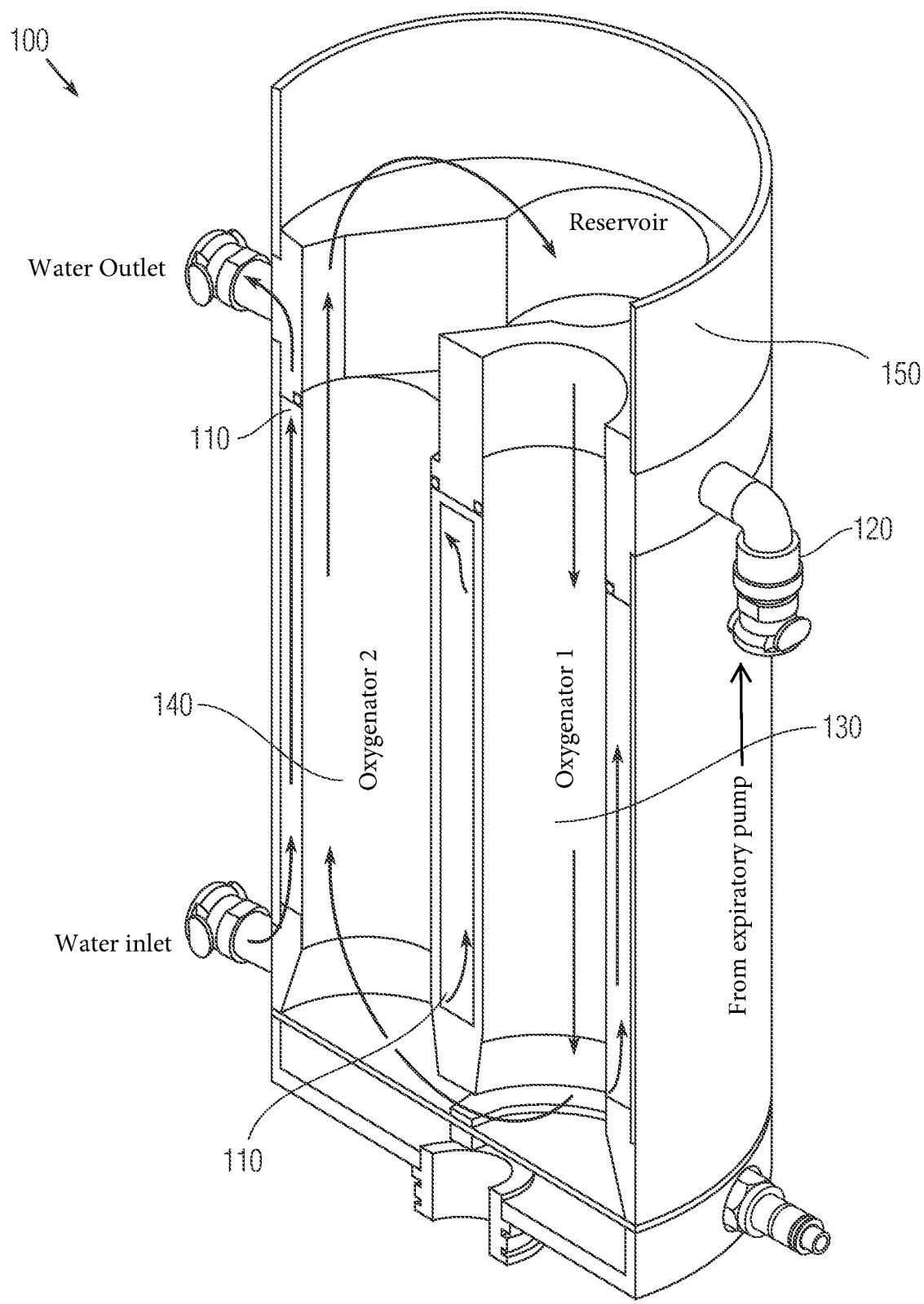
FIG. 1 is a perspective, cutaway view of an exemplary perfluorocarbon treatment unit according to an embodiment of the present invention.

The foregoing and other features will become more apparent upon reading of the following non-restrictive description of illustrative embodiments thereof, given by way of example only with reference to the accompanying drawings. Like numerals represent like features on the various drawings.

A general description of TLV is found in U.S. Pat. No. 7,726,311 B2, "Method and apparatus for conducting total liquid ventilation with control of residual volume and ventilation cycle profile", issued on Jun. 1, 2010 to Robert et al. (hereinafter "Robert'311"), the disclosure of which is incorporated by reference in its entirety.

A contribution of TLV compared to conventional mechanical ventilation in acute respiratory failure is the possibility, by cancelling the air-liquid interface of gas ventilation, to allow expansion and recruitment of alveoli pathological non-compliant with much lower pressures. The risk of volo/barotrauma is significantly reduced, alveolar ventilation is more homogeneous, atelectasis is eliminated and ventilation-perfusion inequality is decreased. TLV has a strong potential for airway washing which, associated with anti-inflammatory properties of PFC, add cyto-protection of the PFC to the pulmonary mechanic protection of TLV.

Additionally, TLV technology can be instrumental in the implementation of moderate therapeutic hypothermia (MTH) or rewarming. Conventional MTH uses various cooling methods, including skin cooling using air, gel packs, refrigerant helmets, cooling blankets, allowing a reduction of body temperature of 0.2° C. to 1° C. per hour. Use of external ice cooling or gastric lavage with an icy saline solution allows accelerating the speed of cooling to 1.6° C. hour. Meeting a MTH temperature set point can take a few hours. For example, it may take two (2) hours for an infant to reach a set point of 34° C. to 35° C. A faster technique, such as direct immersion of the patient in icy water can provide a 10° C. per hour cooling speed, but this technique is not put into practice on anaesthetized and ventilated patients. Alternatively, cooling by intravascular device placed in the inferior vena cava allows reaching cooling speeds of 3° C. to 6° C. per hour, enabling to reach the target temperature in under an hour. Hypothermia induced by extracorporeal circulation is fastest, allowing cooling a patient's body temperature by 15° C. in 30 minutes. Regardless of the technique used to induce hypothermia, it is important to avoid lowering the heart temperature below about 30° C., since such temperatures are known to cause arrhythmia.

PFC may be used as a heat transfer fluid to evacuate body heat using the lungs as a heat exchanger while maintaining normal gas exchange. Therefore, TLV-induced MTH can be very quick and less invasive than ECMO.

The present invention aims at providing improvements in at least one aspect of TLV. One general exemplary purpose of these improvements is to facilitate the deployment and use of the technology in a clinical setting, especially with regards to the associated safety requirements.

A need has been identified for obtaining a measure of tracheal pressure in the context of TLV. For instance, it may be hazardous to provide excessive inspiratory pressure, which could cause respiratory track damage. Expiratory pressures falling below −30 cm $H_2O$ can also lead to collapse of the trachea. As such, and obtaining a measure of tracheal pressure would contribute to alleviate these exemplary risks. Mechanical ventilation methods are based on an estimation of pressure at a patient's mouth using a pressure sensor in the ventilator, compensating for a pressure drop introduced by the ventilator circuit. Since this pressure drop is low in the case of a mechanical ventilator, this provides an acceptable estimate of tracheal pressure. In the case of TLV, a respiratory liquid such as PFC has a high viscosity and twice the density of water, which means that the pressure drop in the endotracheal tube is far more important than in mechanical ventilation, while also being sensitive to fluid acceleration. It has been proposed to either rely on a measure of pressure in the patient's mouth, without factoring pressure losses in the trachea and in an endotracheal tube, or to provide a separate lumen having a tracheal pressure sensor as a part of an endotracheal tube. These methods have not proven to be sufficiently reliable for safe application of TLV on humans.

A need has also been identified for obtaining a measure of lung temperature in the context of TLV, which becomes necessary in certain exemplary use cases such as the ones related to MTH or rewarming.

Various aspects of the present disclosure generally address one or more of the problems related to the lack of maturity of current total liquid ventilation (TLV) technology.

The following terminology is used throughout the present disclosure:

Indirect measurement: calculated value of a condition present at a given location, not directly measured at the given location, based on measurements obtained at another location. The terminology virtual measurement may also be used to refer to an indirect measurement.

Airway pressure: pressure at the level of a patient's trachea or main bronchi.

Lung temperature: temperature at the level of a patient's alveolar, main bronchi and/or lungs.

Total liquid ventilation: a method of providing respiratory support by filling a patient's lungs with a liquid, also known as "liquid breathing".

Perfluorocarbon (PFC): a liquid carbon and fluorine compound in which breathable gas are highly soluble.

Endotracheal tube: a catheter configured for insertion in a patient's trachea. Skilled persons will readily understand that nasotracheal and/or tracheostomy tube may also be used in the context of the present invention.

Distal end: as applied to an endotracheal tube, an end of the tube inserted deep into a patient's trachea.

Proximal end: as applied to an endotracheal tube, an end of the tube connected to other elements of a ventilatory system.

Pressure drop: a difference in pressure between two points of a fluid carrying network.

Resistance: a lumped parameter to model a pressure drop component directly opposed to a fluid flow rate.

Inertance: a lumped parameter to model a pressure drop component directly opposed to an acceleration of the fluid flow rate.

Thermal dead volume: The volume of liquid that does not take part in the thermal exchange in the lungs. The thermal dead volume depends on the anatomic dead space and the volume in the tubes between the patient and the temperature sensor.

Expiratory cycle: phase of a respiratory cycle during which fluid is expelled from the lungs; can include a pause at the end or can precede such a pause, depending on a chosen definition.

Moderate therapeutic hypothermia: a method of medical treatment that involves cooling of a patient's body temperature.

Fast induction of hypothermia by TLV: a method of medical treatment that involves fast cooling of a patient's body temperature while avoiding lowering the heart temperature below about 30° C.

Sensor: a device capable of measuring and converting a physical quantity into a signal; the signal being for example an electrical signal, a radio signal, or a secondary physical representation of the measured physical quantity.

Interface: any communicating element capable of sending or receiving a signal.

Analyzer: an electronic circuit, a computer, a processor, or a calculator, either stand-alone or embedded into a larger machine, capable of processing a signal.

Non-stationary (or unstationary) flow: a time-dependent flow distribution. in the context of the present invention, a non-stationary flow is expected, but a stationary flow or temporarily stationary flow could be present without affecting the present invention.

Clinical use of TLV on human patients requires minimal invasive procedures. Installation of a tracheal pressure sensor for control of inspiratory and expiratory pressures, installation of an esophageal temperature sensor, or installation of a femoral arterial temperature sensor for control of body temperature, should all be avoided. Rectal, esophageal or tympanic temperature measurements have long time constants and are not reliable to avoid lowering the heart at a temperature below about 30° C. during fast induction of moderate therapeutic hypothermia (MTH). To this end, the present disclosure introduces the concept of indirect measurement of pressure and temperature in the context of total liquid ventilation. Skilled person will readily recognize that the general principle may also be used in the context of rewarming.

Referring now to the drawings, FIG. 1 is a perspective, cutaway view of a perfluorocarbon treatment unit. An integrated PFC treatment unit (IPTU) 100 has a PFC heat exchanger system including double walls 110 and a heat transport fluid (liquid or gas) 160 flowing between the walls 110. The double walls 110 are made of thin (for example 0.020 inch) stainless steel. PFC from a patient's lungs enters the IPTU 100 via an inlet conduit 120. PFC transits through a first oxygenator 130 and a second oxygenator 140 before reaching a reservoir 150. The PFC then flows from the reservoir 150, through an outlet (not shown), towards the patient's lungs. A condenser and a gas mixer are not shown. Owing to good thermal exchange capabilities of the double walls 110, the IPTU 100 can heat or cool the PFC in order to elevate or lower the temperature of a patient under TLV. Oxygen bubbles formed with the oxygenators 130 and 140 tend to favor PFC temperature uniformity within the oxygenators 130 and 140, which in turn optimizes heat transfer between the PFC and the heat transport fluid.

Figure 2:
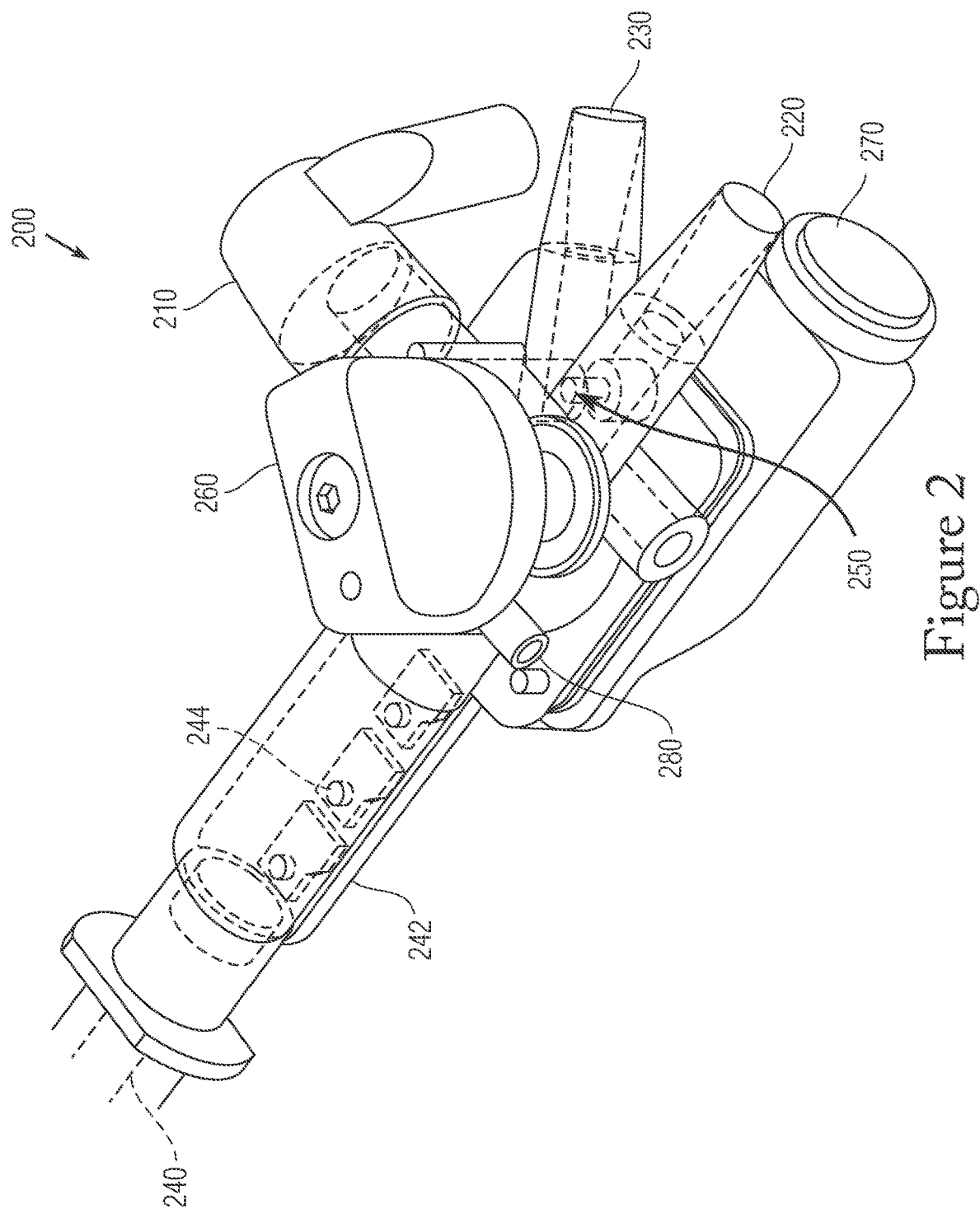
FIG. 2 is a detailed, perspective view of an exemplary Y-connector according to an embodiment of the present invention.

FIG. 2 is a detailed, perspective view of a Y-connector according to an embodiment. A Y-connector 200 comprises an aerial port 210 for connection to a conventional mechanical ventilator, an inspiratory liquid port 220 for receiving PFC from the IPTU 100, an expiratory liquid port 230 for returning PFC toward the inlet conduit 120 of the IPTU 100, an endotracheal tube (ETT) port 240 for connection of an ETT (shown on later Figures) or any tube that give access to the patients trachea or main airways/respiratory tract, a PFC temperature sensor 250, and a three-way valve 260 allowing a user to select between mechanical ventilation or TLV by either connecting the aerial port 210, or both the liquid ports 220 and 230, to the ETT port 240. The ETT port 240 comprises a parietal pressure sensor 244 and a flow meter 242. The three-way valve 260 may be equipped with light emitting diodes (LED) providing a visual indication of a selected valve position. The PFC temperature sensor 250, the parietal pressure sensor 244 and the flow meter 242 are operably connected to a communication port 270 that provides an interface for outputting temperature, pressure and flow measurements of the PFC towards an analyzer (shown on later Figures). In a first variant, the measurements can be provided as numerical information elements, output from the communication port 270 by wired or wireless connection. In a second variant, a capillary may be attached to the side port 280, pressure measurements being obtained remotely at a distal end of the capillary. Flow measurements may be taken in inspiratory and/or expiratory PFC conduits located between the Y-connector 200 and the IPTU 100. In the depicted example, all the sensors in the Y-connector are collocated.

Figure 3:
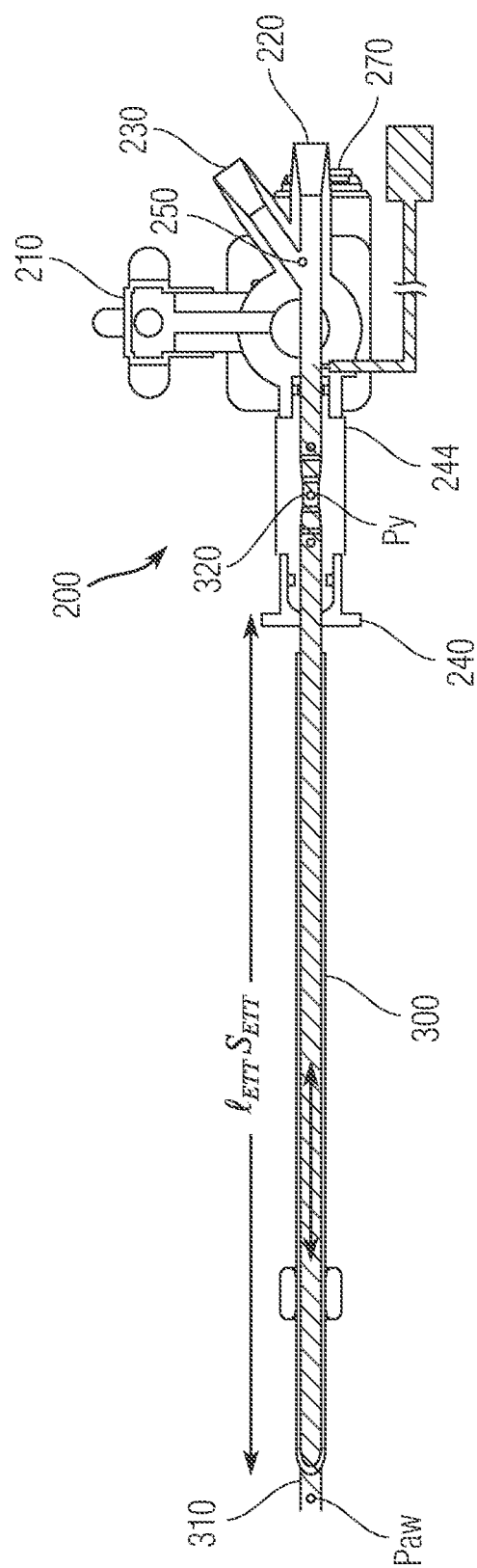
FIG. 3 is an example of Y-connector coupled to an exemplary endotracheal tube according to an embodiment of the present invention.

FIG. 3 is an example of Y-connector coupled to an endotracheal tube. An endotracheal tube (ETT) 300 is mounted to the ETT port 240 of the Y-connector 200. Other connections to the ports 210, 220 and 230 are not shown, but are self-explanatory. A distal end 310 of the ETT 300 is located at the trachea, where it is clinically required to determine an airway pressure ($P_{aw}$). Moreover, it is clinically required to estimate the lung temperature at the alveoli, which is even deeper into the lungs than the patient's trachea. It may be observed that the lung temperature is a good approximation of the blood temperature exiting the lungs, which is the final objective. Rather than inserting a pressure sensor at a level of the patient's trachea, at or near the distal end 310, pressure measurements within the Y-connector 200 at a proximal end 320 of the ETT 300 are used to obtain relevant indirect pressure values. A section $S_{ETT}$ and a length $L_{ETT}$ of the ETT 300 are known and are used in calculations of the $P_{aw}$. $P_{aw}$ is derived from a pressure measurement $P_y$ taken directly at the proximal end 320. Rather than inserting a temperature sensor at the alveolar level in the lungs, temperature measurements within the Y-connector 200 at a proximal end 320 of the ETT 300 are used to obtain relevant indirect temperature values.

One set of embodiments of the present invention generally relates to indirect pressure measurements.

Expired PFC is conditioned in the IPTU 100, where the PFC temperature is also controlled. PFC reaches the Y-connector 200 at the inspiratory liquid port 220 and flows to the lungs via the ETT 300, returning from the lungs via the ETT 300 and returning to the IPTU 100 via the expiratory liquid port 230.

A representation $\hat{P}_{aw}$ that provides an estimation of the actual airway pressure $P_{aw}$ at the distal end 310 of the ETT 300 is obtained from a parietal pressure $P_y$ measured at the proximal end 320 of the ETT 300, using the parietal pressure sensor 244 of the Y-connector 200. A flow ($\dot{V}$) of the PFC, which is a variation of a PFC volume (V) within the lungs of the patient, is measured using the flow meter 242 or using a sensor coupled to inspiratory or expiratory conduits present between the Y-connector 200 and the IPTU 100. $P_{aw}$ is estimated based on the measure of $P_y$, accounting for a pressure drop $\Delta P(\dot{V})$ calculated on the basis of the flow of PFC ($\dot{V}$) into the tube:

$$\hat{P}_{aw}(\dot{V}) = P_y + \Delta P(\dot{V}) \qquad (1)$$

wherein:

$$\Delta P(\dot{V}) = -R_1 \dot{V} - \text{sgn}(\dot{V})(R_2 \dot{V}^2) \qquad (2)$$

in which the parameters $R_1$ and $R_2$ depend on the length $L_{ETT}$ and section $S_{ETT}$ of the ETT 300, and wherein $\text{sgn}(\dot{V})$ is the sign function. In the case of strong acceleration or deceleration of flow($\dot{V}$), which is the case for unsteady flow, calculation of $P_{aw}$ can further include an acceleration of the flow ($\ddot{V}$), such that:

$$\Delta P(\dot{V}) = -R_1 \dot{V} - \text{sgn}(\dot{V})(R_2 \dot{V}^2) + I\ddot{V} \qquad (3)$$

or, in a more general form:

$$\hat{P}_{aw} = P_y + g(\dot{V}, \ddot{V}, T_y) \qquad (4)$$

wherein $g(\dot{V}, \ddot{V})$ represents an analytical mapping produced as a function of parameters related to resistances ($R_1$, $R_2$) of the ETT 300 and to an inertance (I) of the liquid in the ETT 300, as obtained from in vitro measurements or from an unsteady Bernoulli's equation, or from any other fluid mechanic relation capable of linking a pressure differential $\Delta P$ between two specific points. The resistance terms $R_1$ and $R_2$ can also include the patient's lung resistance. In this specific case, the pressure estimated is the alveolar pressure and it can also be used by the pump controllers to command the pumps.

The PFC flow measurements can be obtained by the flow meter 242 of the Y-connector 200, which is able to identify a direction of flow. Depending in the type of sensor used for the flow determination, periodic calibration of the flow meter 242 should be made using an external (atmospheric) pressure sensor. For instance, periodic calibration may be required for certain types of flow meter such as a pressure flow meter.

Capabilities of the Y-connector 200 to properly estimate airway pressure $P_{aw}$, using the above mathematical model, have been validated both during in-vitro test and in in-vivo experiments on newborn lambs, some of which having healthy lungs in normothermia or hypothermia, other suffering from meconium aspiration syndrome. These experiments were conducted using various type of PFC at different pulmonary volumes.

TLV relies on a pressure regulated expiration that requires an accurate $P_{aw}$ estimation in real-time. The pressure sensor provides the estimate $\hat{P}_{aw}$ of the actual airway pressure in real-time. It enables a controller of the liquid ventilator to adjust in real-time an expiratory flow rate according to a targeted airway expiratory pressure directly specified by the clinician on a user interface or by an algorithm. The same approach can be applied to the inspiration phase of the respiration cycle. The airway pressure estimate $\hat{P}_{aw}$ can be used by an inspiration pressure controller which maintains the airway pressure at the required reference specified by the clinician on the user interface or by an algorithm. This inspiration pressure controller is also used during the initial lung filling. It avoids lung overpressure by maintaining a constant pressure during the PFC instillation in the lungs, when air is still present.

Figure 4:
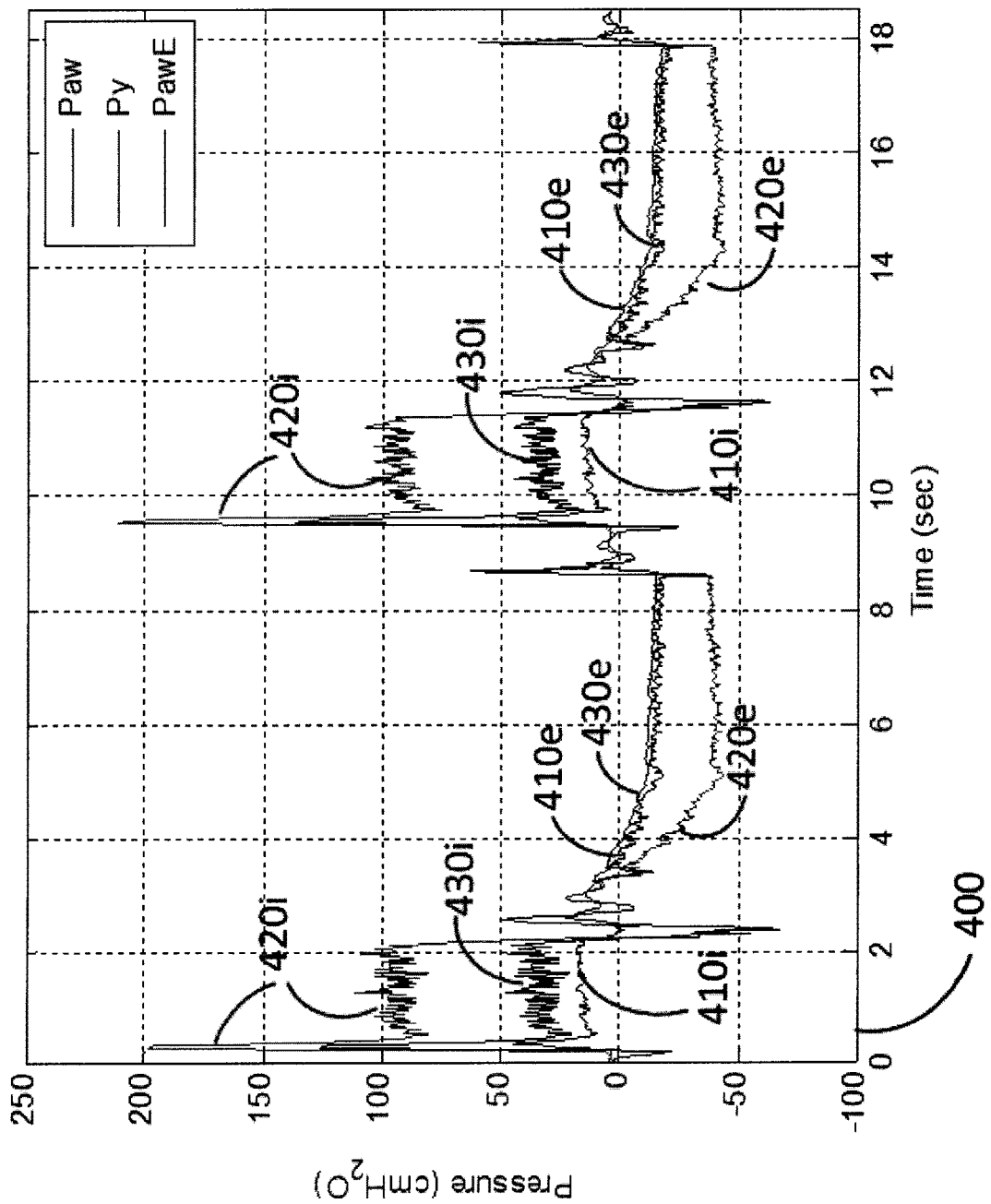
FIG. 4 is a graph showing exemplary pressure measurements obtained from a lamb under total liquid ventilation according to an embodiment of the present invention.

FIG. 4 is a graph showing pressure measurements obtained from a lamb under total liquid ventilation. A graph 400 shows pressure traces, as a function of time, obtained while subjecting a lamb to TLV. The traces include actual airway pressure ($P_{aw}$) 410*i* (inspiration) and 410*e* (expiration), a parietal pressure ($P_y$) 420*i* and 420*e* measured at the Y-connector 200, and an estimated ($\hat{P}_{aw}$) 430*i* and 430*e*. During expiration, the $\hat{P}_{aw}$ 430 is used to control the expiratory flow. Due to the measurement method, the measure of $P_{aw}$ is incorrect during inspiration.

Figure 5:
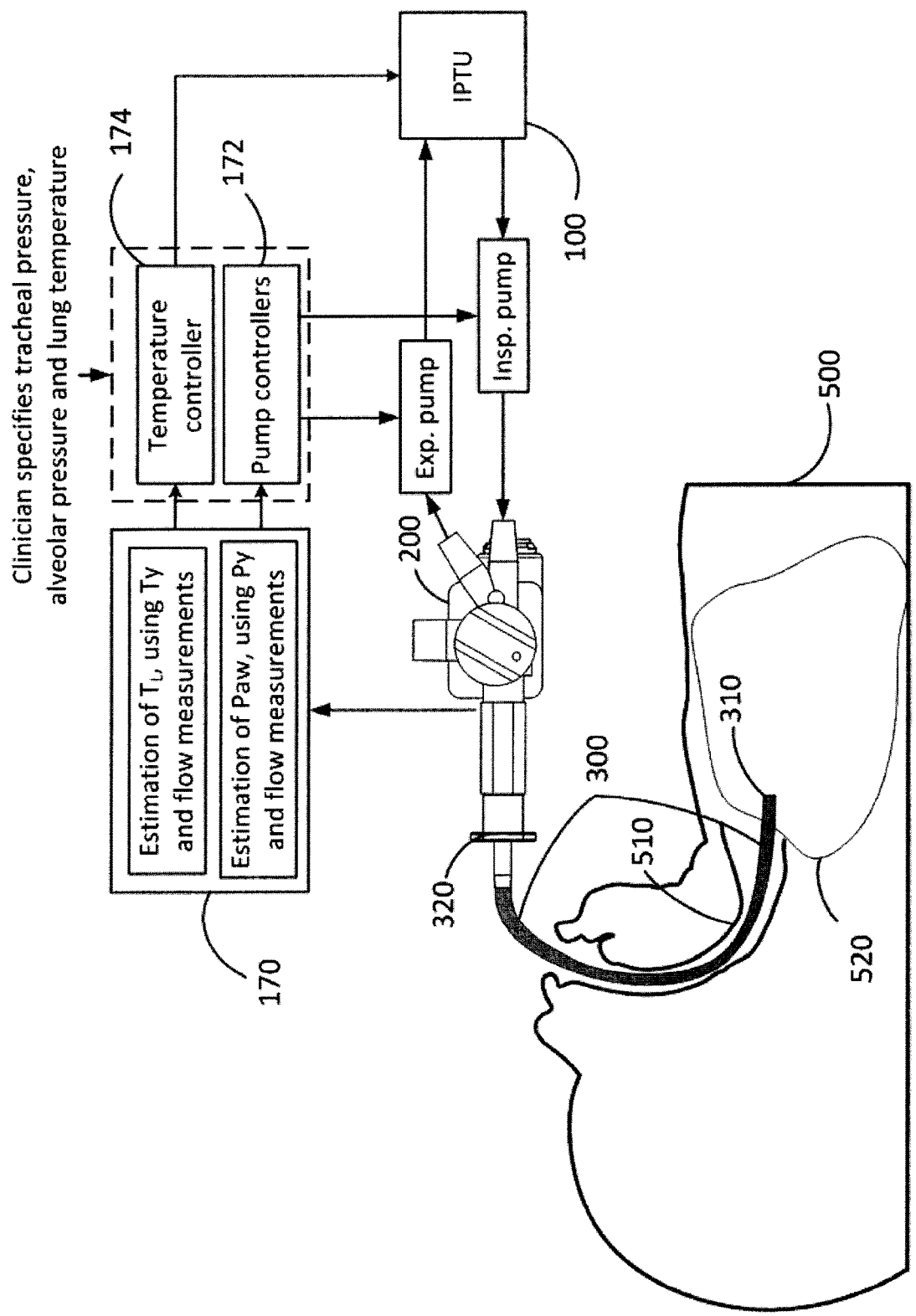
FIG. 5 is a view of a patient receiving total liquid ventilation via an exemplary endotracheal tube and the exemplary Y-connector of FIG. 2, according to an embodiment of the present invention.

FIG. 5 is a first view of an infant patient receiving total liquid ventilation via an endotracheal tube and the Y-connector of FIG. 2. This Figure summarizes an application of TLV for care of an infant 500. The ETT 300 is inserted into a trachea 510 of the infant 500, the distal end 310 being located just above the carina, in close proximity to the infant's lungs 520. The proximal end 320 is connected to the Y-connector 200, which in turn is connected to inspiratory and expiratory circuits of the IPTU 100. An analyzer 170 receives the parietal pressure $P_y$, flow ($\dot{V}$) and flow acceleration ($\ddot{V}$) measurements and calculates the estimated airway pressure $\hat{P}_{aw}$. It also receives the temperature $T_y$, flow ($\dot{V}$) and flow acceleration ($\ddot{V}$) measurements and calculates the estimated lung temperature $T_L$. A pump controller 172 of the TLV system controls the pumps (not shown) of the liquid ventilator based on the estimated airway pressure $\hat{P}_{aw}$ and on tracheal and alveolar pressure set-points defined by a clinician. A temperature controller 174 of the TLV system controls the temperature of the PFC inside the IPTU 100, based on the estimated lung temperature $T_L$. Feedback loops are thus formed between the sensors in the Y-connector 200, the analyzer 170, and the controllers (172 and 174), so that a body temperature of the infant 500 and the airway pressure can be controlled according to the set-point entered by the clinician.

Figure 6:
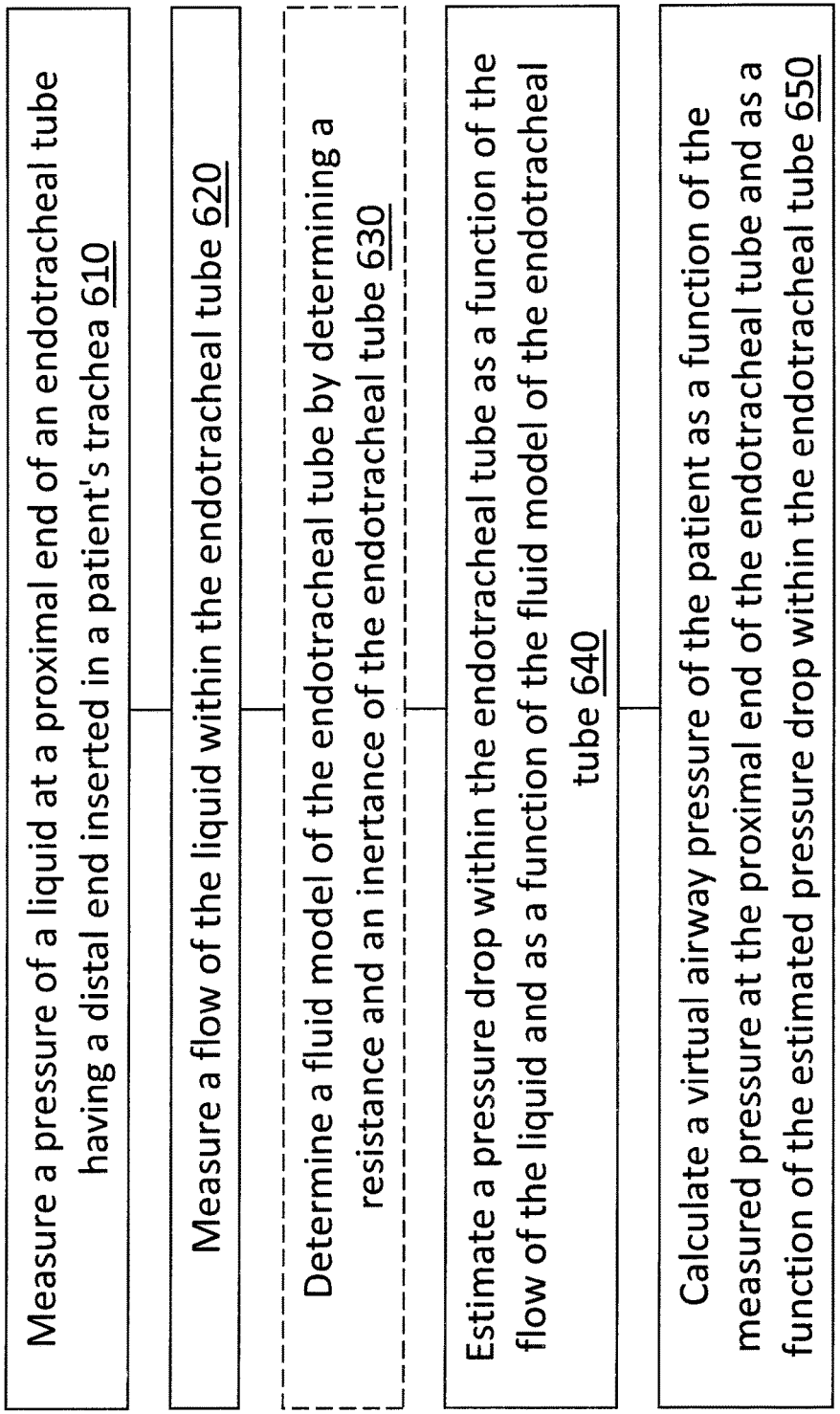
FIG. 6 is a sequence diagram showing operations of an exemplary method for indirect tracheal pressure measurement using a total liquid ventilation system according to an embodiment of the present invention.

FIG. 6 is a sequence diagram showing operations of a method for tracheal pressure measurement using a total liquid ventilation system. In FIG. 6, a sequence 600 comprises a plurality of operations that may be executed in variable order, some of the operations possibly being executed concurrently, some of the operations being optional. In operation 610, a pressure of a liquid is measured at the proximal end 320 of the endotracheal tube 300 having its distal end 310 inserted in the trachea 510 of a patient, for example the infant 500, or in a trachea of an animal. Without limitation, the liquid may carry oxygen or carbon dioxide. A flow of the liquid within the endotracheal tube 300 is measured in operation 620. Optionally, operation 630 comprises determining a fluid model of the endotracheal tube 300 by determining a resistance of the endotracheal tube 300 and an inertance of the liquid the endotracheal tube 300. Operation 640 comprises an estimation of a pressure drop within the endotracheal tube 300 as a function of the flow of the liquid and as a function of a known or estimated fluid model of the endotracheal tube 300. The airway pressure of the patient is calculated at operation 650 as a function of the measured pressure at the proximal end 320 of the endotracheal tube 300 and as a function of the estimated pressure drop within the endotracheal tube 300.

Figure 7:
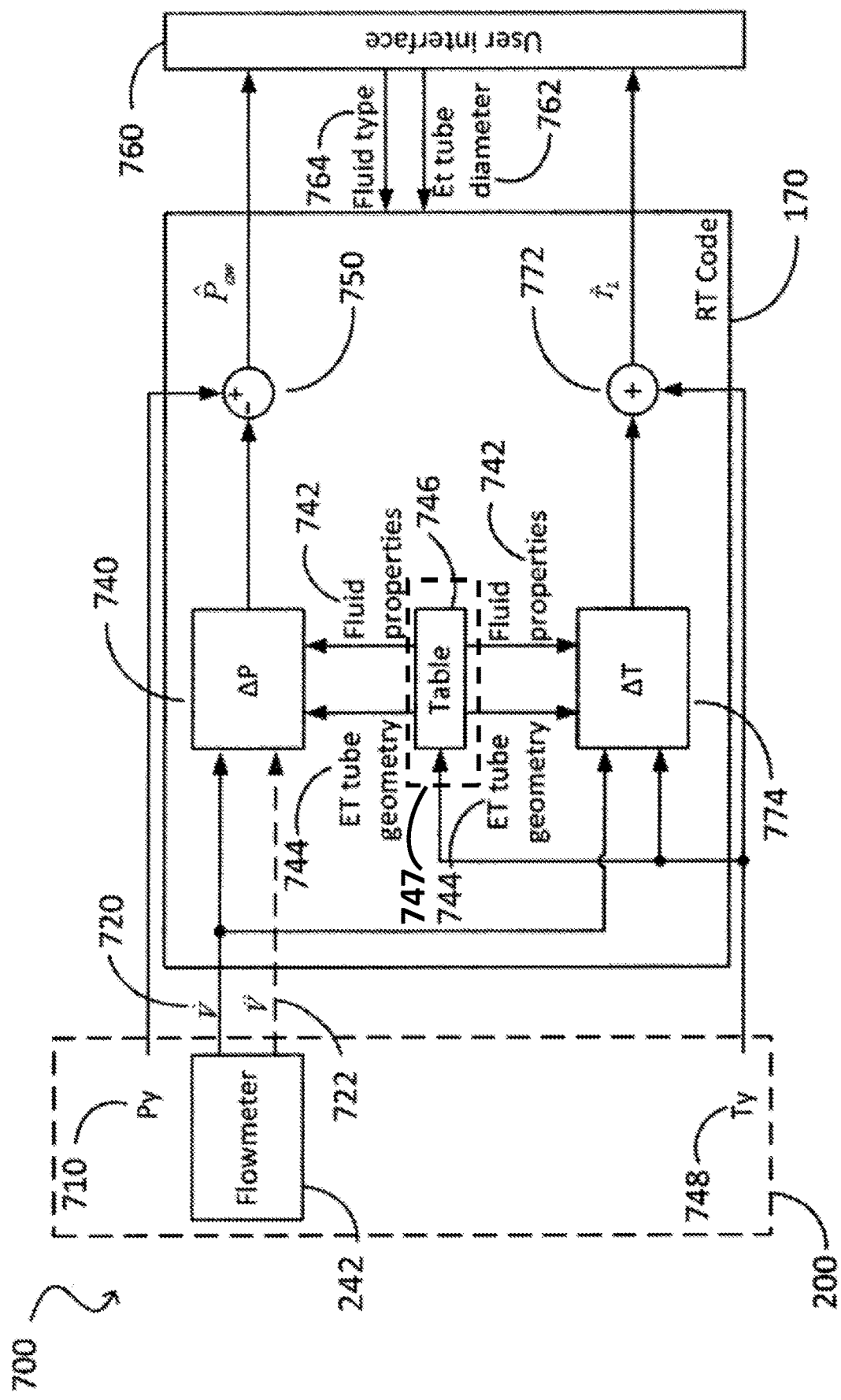
FIG. 7 is a block diagram of an exemplary system for indirect airway pressure and/or indirect lung temperature measurements using a total liquid ventilation system according to an embodiment of the present invention.

FIG. 7 is a block diagram of a system for airway pressure measurement and lung temperature measurement using a total liquid ventilation system. In FIG. 7, a system 700 comprises a plurality of components, some of which may be optional. A fluid pressure 700 ($P_y$) and temperature 748 ($T_y$) are measured by the pressure sensor 244 and a temperature sensor 250 at the proximal end 320 of the endotracheal tube 300 having its distal end 310 inserted in the trachea 510 of a patient. The flow meter 242 measures a fluid flow 720 ($\dot{V}$) and its derivative 722 ($\ddot{V}$) within the endotracheal tube 300. On a user interface 760, the user select a fluid type 764 and a diameter 762 of the ETT 300 inserted into the patient's trachea. These information elements are provided to the analyzer 170.

The analyzer 170 uses a fluid model of the flow and a temperature model in the ETT 300 to estimate a pressure drop ΔP and a temperature difference ΔT within the ETT 300. In an embodiment, the fluid model includes a resistance and an inertance of the ETT 300. In the same or in another embodiment, the fluid model and temperature model may be based on a tube geometry 744 and on fluid properties 742. The fluid type 764, the diameter 762 of the ETT 300 and, optionally, a fluid temperature 748 measured for example at the temperature sensor 250 of the Y-connector 200, are used to determine the fluid properties 742 and the tube geometry 744. In a variant, a look-up table 746 stored in a memory module 747 of the analyzer 170 may be used to obtain the fluid properties 742 and the tube geometry 744 based on the fluid type 764, on the diameter 762, and on the fluid temperature 748. The fluid properties 742 and the tube geometry 744 are fed to an estimator of the pressure drop ΔP 740 and of the temperature difference ΔT 774 within the ETT 300. The estimator 740 uses the liquid flow rate 720 ({dot over (V)}) and its derivative 722 ({umlaut over (V)}) along with the fluid model to estimate the pressure drop ΔP. The airway pressure {circumflex over (P)}aw of the patient is calculated at an adder 750 as a function of the measured pressure 710 (Py) obtained at the proximal end 320 of the ETT 300 and as a function of the estimated pressure drop ΔP within the ETT 300. The airway pressure {circumflex over (P)}aw of the patient may be displayed on the user interface 760 may be also be used by the pump controller 172 of the TLV system. The estimator 774 uses the liquid flow rate 720 ({dot over (V)}) along with the thermal model to estimate the temperature difference ΔT. The lung temperature of the patient is calculated at an adder 772 as a function of the measured temperature 748 (Ty) obtained at the proximal end 320 of the ETT 300 and as a function of the estimated temperature difference ΔT within the ETT 300. The lung temperature {circumflex over (T)}L of the patient may be displayed on the user interface 760 and may also used by the temperature controller 174 of the TLV system.

One set of embodiments of the present invention generally relates to indirect temperature measurements.

Figure 8:
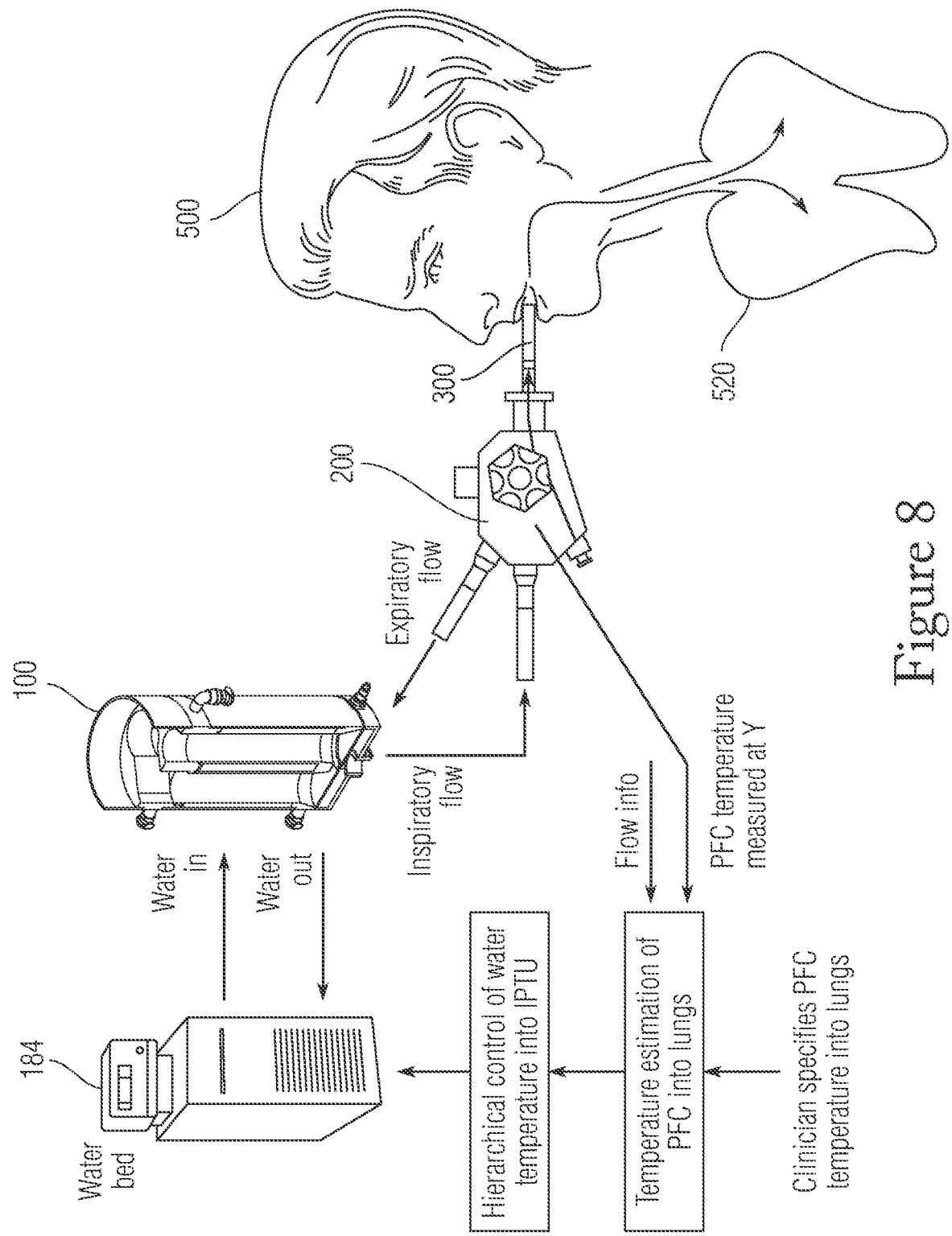
FIG. 8 is a view of a patient receiving total liquid ventilation via an exemplary endotracheal tube and the exemplary Y-connector of FIG. 2, also showing the exemplary perfluorocarbon treatment unit of FIG. 1, according to an embodiment of the present invention.

FIG. 8 is a second view of an infant patient receiving total liquid ventilation via an endotracheal tube and the Y-connector of FIG. 2, also showing the perfluorocarbon treatment unit of FIG. 1. In FIG. 8, the infant 500 is subject to a MTH or rewarming procedure. The temperature sensor 250 of the Y-connector 200 provides a real-time measurement of the PFC expelled from the lungs 520 of the infant via the ETT 300. A clinician provides a temperature set-point for the PFC temperature, according to a desired level of hypothermia (of course, a similar procedure can be applied when it is desired to raise a body temperature of the infant 500). An analyzer 170 receives the temperature set-point, the real-time PFC temperature measurement, and may further receive a flow measurement from the flow meter 244 of the Y-connector or from any other flow meter within the TLV system. The analyzer 170 selects temperature measurements obtained, for example, during an expiratory phase, at the end of expiratory flows, or during a pause following each expiratory cycle. The analyzer 170 provides temperature commands to a temperature controller 174 that, in turn, controls a water bed or water bath 184. The water bed 184 supplies water, or any other heat transport fluid (liquid or gas) 160 that flows between the walls 110 of the IPTU 100. A feedback loop is thus formed between the temperature sensor 250, the analyzer 170, the temperature controller 174, the water bed 184 and the IPTU 100 so that a body temperature of the infant 500 can be controlled according to the set-point entered by the clinician. Skilled readers will readily understand that the water bath 184 is one of many options that may be used to achieve at least some level of cooling or heating in the system. For instance, the water bath 184 can be replaced by other cooling and/or heating devices such as an evaporator (from a compressor circuit) put in direct contact with the liquid or using a gas expansion device (i.e., propane refrigerator). Other solutions may also be used such as thermoelectric modules, which could control the PFC temperature. Also, prior to its use, the PFC can be cooled inside a refrigerator (for example) in which an additional heating element may also be used to control the liquid temperature. Other solutions may include using phase changing materials, ice, solar energy, fossil fuels or vortex tubes as a cooling and heating sources to manage the PFC temperature.

A representation $\hat{T}_L$ that provides an estimation of the actual alveolar temperature is obtained from a temperature 748 ($T_y$) measured at the proximal end 320 of the ETT 300 on the Y-connector 200. A flow 720 ($\dot{V}$) of the PFC is measured using the flow meter 244 or using a sensor coupled to inspiratory or expiratory conduits present between the Y-connector 200 and the IPTU 100.

$$\hat{T}_L(\dot{V}) = T_y + \Delta T(\dot{V}) \tag{5}$$

wherein:

$$\Delta T(\dot{V}) = \Delta T_y \frac{\tau(\dot{V})}{\delta} \tag{6}$$

in which the time constant (τ) depends on the temperature sensor 250, the liquid properties given by the table 746 and the flow 720 ($\dot{V}$). The time constant (τ) represents an analytical mapping produced as a function of the parameters related to the temperature sensor 250, the liquid properties and the flow 720 ($\dot{V}$), as obtained from in vitro measurements, from forced convection equation, or from any other thermodynamic relations.

The temperature sensor 250 of Y-connector 200 allows obtaining an estimate of the temperature of the lungs that can be assumed to be in equilibrium with a temperature of the blood in the pulmonary veins and a temperature of the heart, also being in approximate equilibrium with femoral arterial temperature. The TLV set up of FIG. 8 thus allows rapid induction of hypothermia under control of the clinician.

Using the same thermal model, the patient's organ temperature (kidney, liver, brain, pancreas, etc.) can also be determined by calculating a temperature difference ΔT between the $T_y$, using the flow in the Y-connector, the blood flow (which could be estimated by the patient's weight indicated on the user interface, or by a direct measurement). In a table 746, the fluid properties of the different liquids in the thermal model can be indicated and the organ perfusion ratio (based on total blood flow) could also be listed. All this information can be used to calculate a time constant τ for estimating the targeted organ temperature based on the equations presented.

Figure 9:
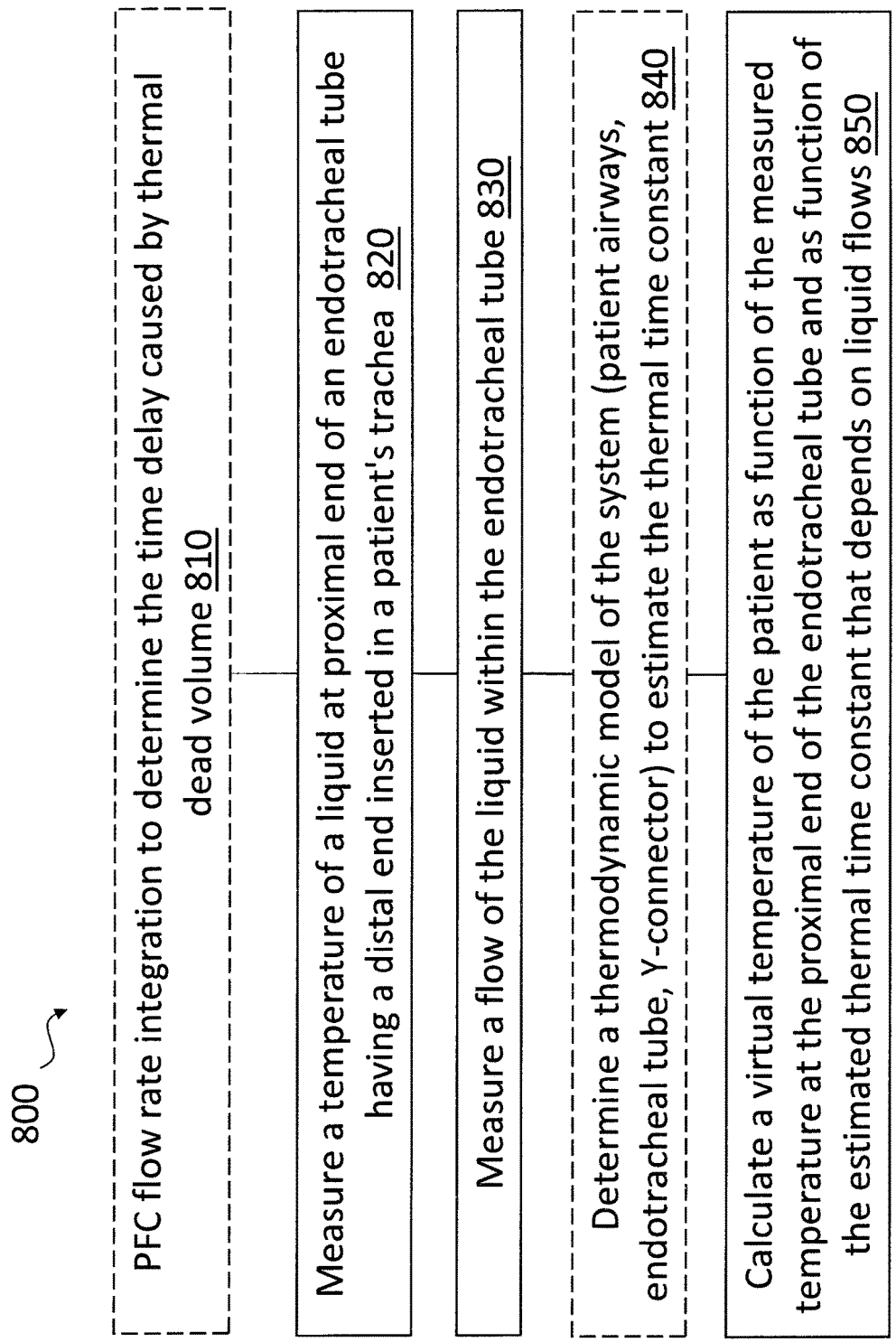
FIG. 9 is a sequence diagram showing operations of a method for indirectly measuring lung temperature using a total liquid ventilation system according to an embodiment of the present invention.

FIG. 9 is a sequence diagram showing operations of a method for lung temperature measurement using a total liquid ventilation system. In FIG. 9, a sequence 800 comprises a plurality of operations that may be executed in variable order, some of the operations possibly being executed concurrently, some of the operations being optional. In operation 810 flow while expiratory cycle is mathematically integrated to determine the time delay caused by the thermal dead volume. A temperature of a liquid expelled from the patient's lungs via an endotracheal tube having an end inserted in the patient's trachea is measured in operation 820. The measurement may for example be obtained at or near the proximal end 320 of the ETT 300 when the distal end 310 is inserted in the trachea 510 of the infant 500, or in a trachea of an animal. In operation 830, flow is measured within the endotracheal tube while expiratory cycle. Operation 840, comprises an estimation of a temperature difference as a function of the flow of the liquid and as a function of a known or estimated thermodynamic model of the system (patient airways, endotracheal tube, Y-connector) to estimate thermal time constant. The lung temperature of the patient is calculated at operation 850 as a function of the measured temperature at the proximal end 320 of the endotracheal tube 300 and as a function of the estimated thermal time constant of the system. The measured temperature of the liquid can be used as a lung temperature measurement, at operation 830, for controlling a moderate therapeutic hypothermia of the patient. In operation 810, the expiration flow is mathematically integrated until the exhaled volume becomes greater than the thermal dead volume. The resulting integration period is considered as the time delay caused by the thermal dead volume during which the system may inadequately estimate lung temperature. Other methods could be used to determine the time delay, such as the temperature variation monitoring of the indirect temperature measurements.

Figure 10:
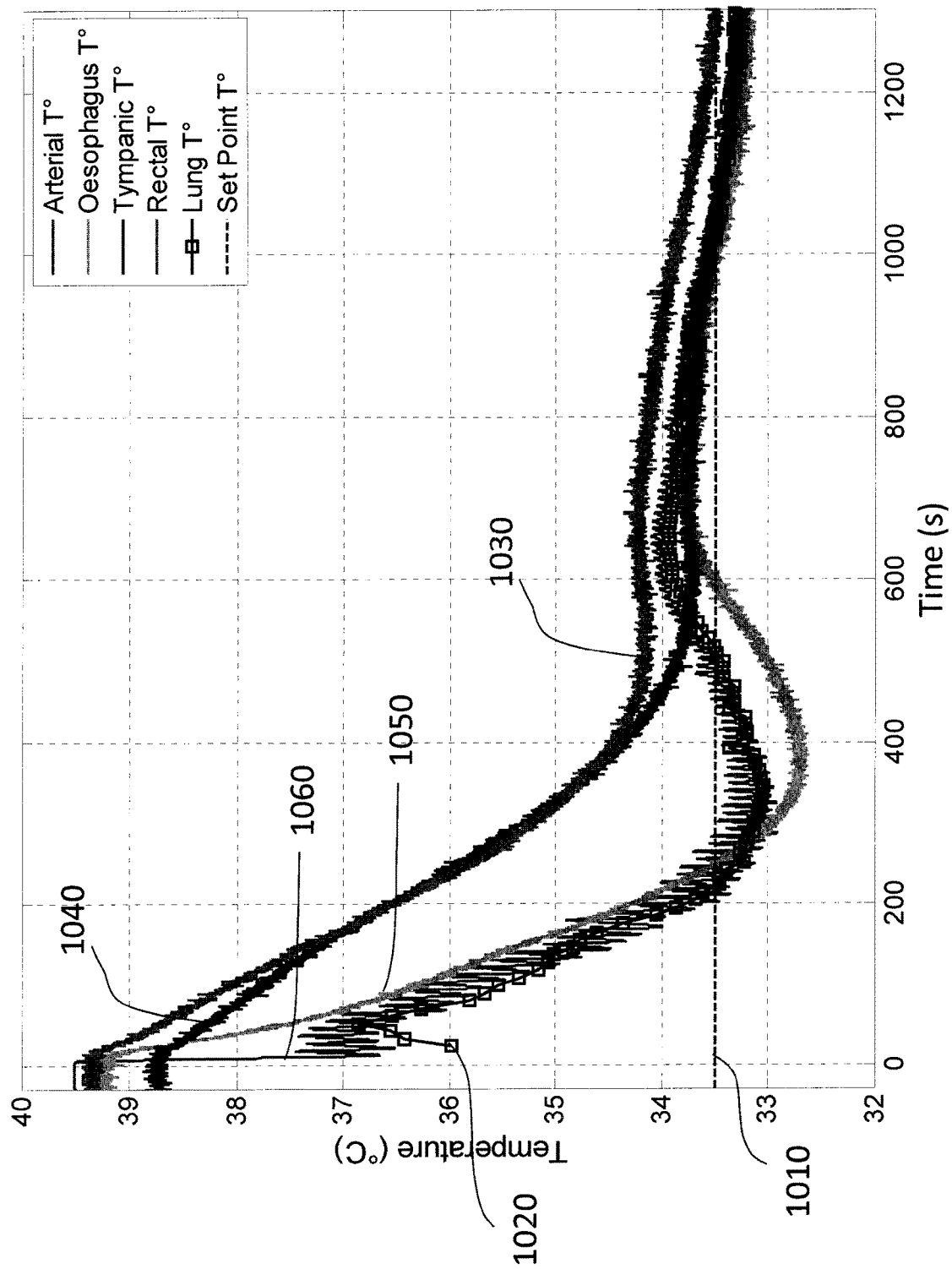
FIG. 10 is a graph showing exemplary temperature measurements obtained from a lamb during induction of Moderate Therapeutic Hypothermia (MTH) according to an embodiment of the present invention.
Figure 11:
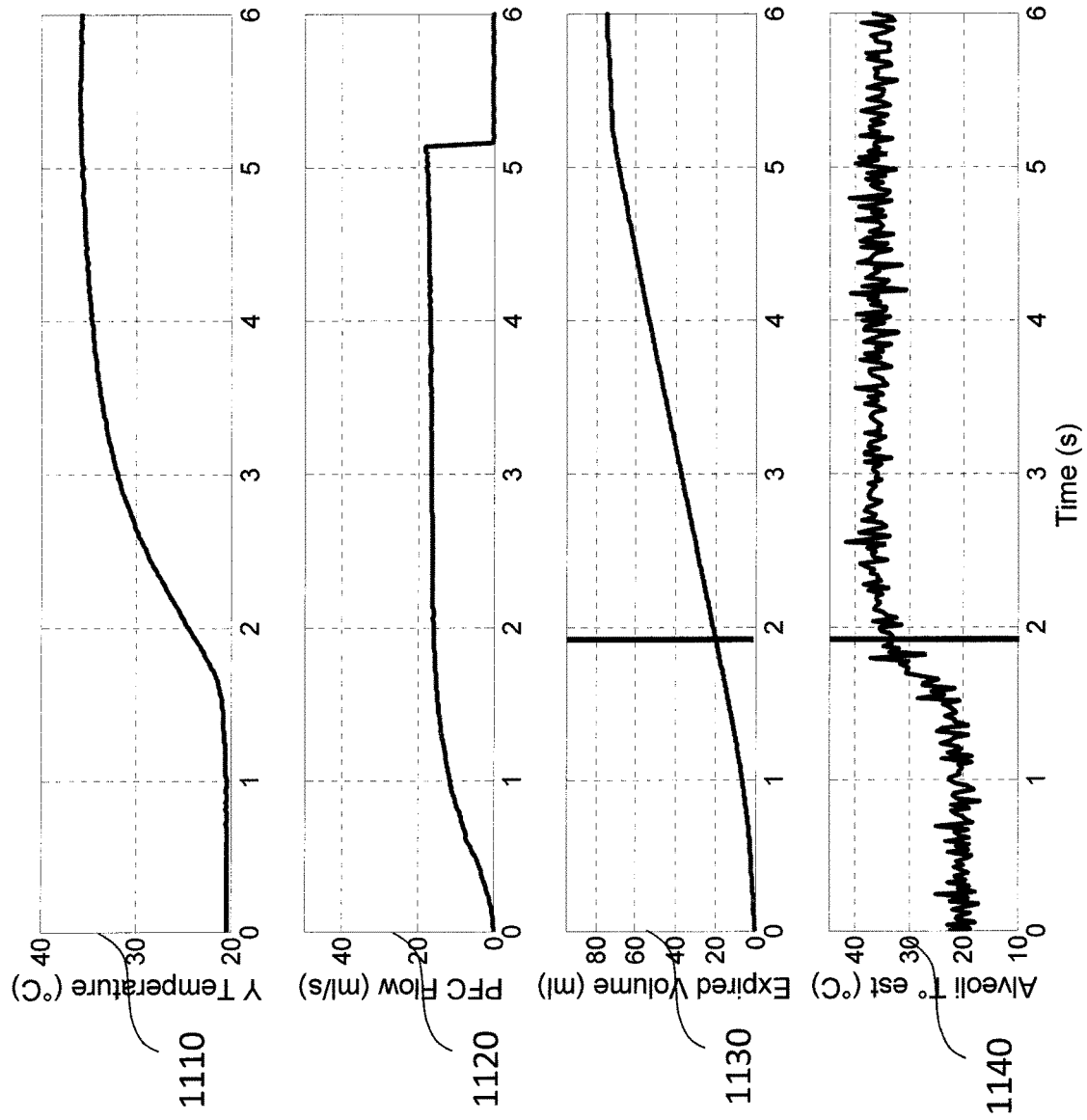
FIG. 11 is a series of graphs showing exemplary temperature measurements, PFC flow measurements, expired volume calculations and lung temperature estimations obtained from a lamb during one expiration during induction of moderate therapeutic hypothermia according to an embodiment of the present invention.
Figure 12:
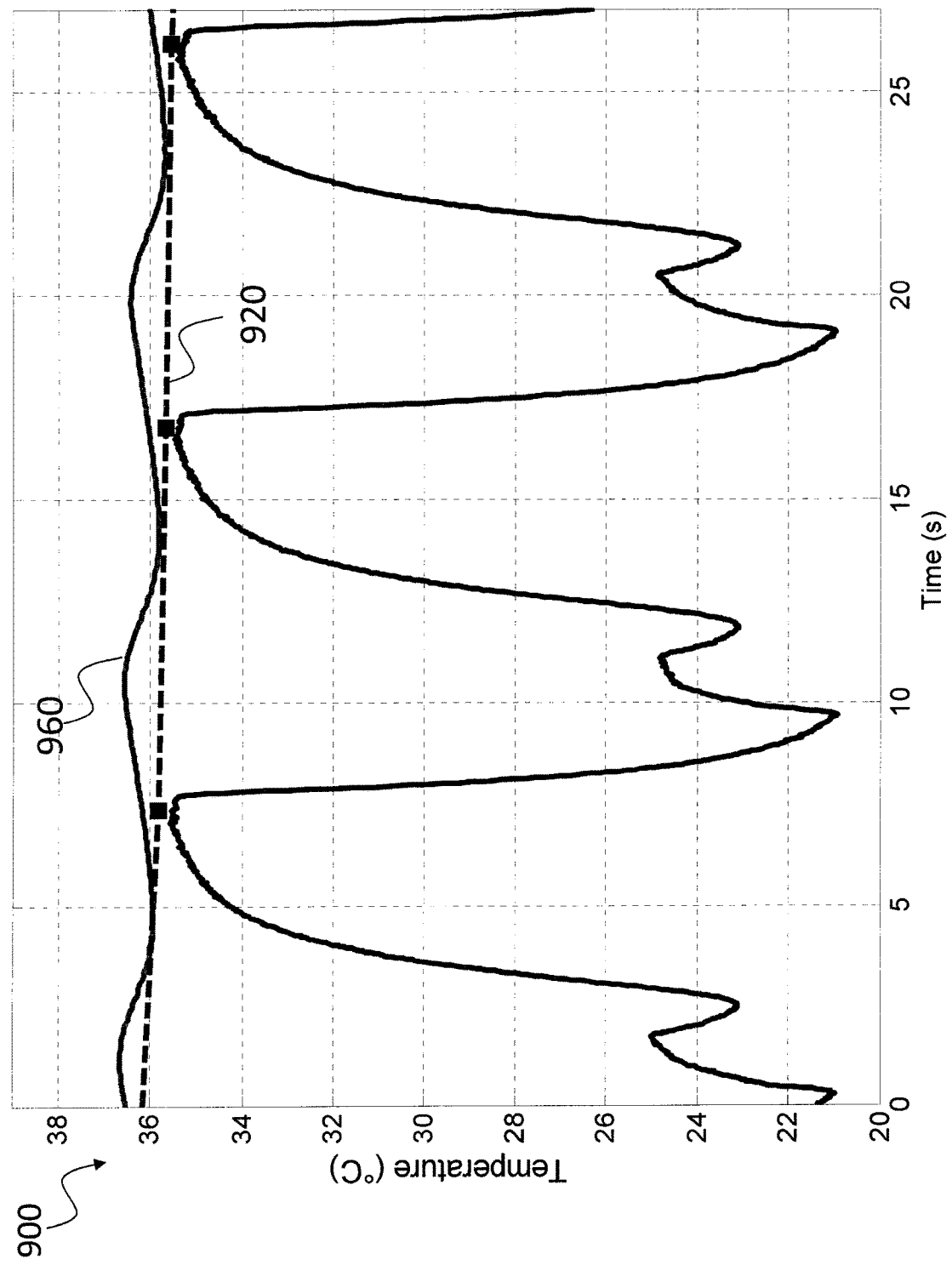
FIG. 12 is a graph showing exemplary arterial temperature measurements, Y-connector temperature measurements and lung temperature estimations obtained from a lamb during induction of moderate therapeutic hypothermia according to an embodiment of the present invention.

The method of FIG. 9 has been tested in-vivo on healthy lambs, as a part of experiments related to ultrafast MTH induction. The lung temperature measurements were compared to direct measurements of the femoral arterial temperature. The results confirm the ability of this method for the rapid induction of the MTH by TLV. FIG. 10 shows a graph of temperature measurements obtained from a lamb during induction of moderate therapeutic hypothermia according to an embodiment of the present invention. On the example of FIG. 10 are represented a setpoint 1010 and measurements/indirect measurements for lung temperature 1020, rectal temperature 1030, tympanic temperature 1040, esophagus temperature 1050 and arterial temperature 1060. FIG. 11 shows temperature measurements 1110, PFC flow measurements 1120, expired volume calculations 1130 and lung temperature estimations 1140 obtained from a lamb during one expiration during induction of moderate therapeutic hypothermia. FIG. 12 shows temperature measurements obtained from a lamb under moderate therapeutic hypothermia. A graph 900 shows three TLV cycle during an experimentation on lamb. It can be observed that the mean lung temperature estimations 920 closely matches the arterial temperature 960.

Though the foregoing description of methods, sensors and Y-connector have been provided with reference to PFC, this technology is readily applicable to any other fluid used in TLV applications. It is expected that TLV, with or without MTH, can provide alternative treatment for infants that cannot receive extracorporeal membrane oxygenation (ECMO). TLV is also expected to evolve so that it becomes applicable to adult patients, and to the treatment of acute respiratory distress syndrome (ARDS) in intensive care. Rapid induction of MTH in out-of-hospital emergency care is also contemplated.

Various embodiments of the methods, connector and TLV systems, as disclosed herein, may be envisioned. One such embodiment comprises a model of a fluid circuit of a total liquid ventilator system. Calculation of $P_{aw}$ can be obtained as a function of present and past data of the flow rate ($\dot{V}$) recorded at a sampling time $\delta$ such that:

$$\hat{P}_{aw}[k]=P_y[k]+g(\dot{V}[k],\dot{V}[k-1],\ldots \dot{V}[k],\ddot{V}[k],\dddot{V}[k-1],\ldots,\dot{V}[k-M],T_y[k]) \quad (7)$$

where k is a discrete time index such that $\dot{V}[k]$ is a present value and $\dot{V}[k-i]$ are past values, for i=1 to M. Also, equation (7) is equivalent to equation (4) and one can uses a history of the flow rate to compute the acceleration and its derivatives, the estimate of $\hat{P}_{aw}$ being then based on measurements $P_y[k]$.

Calculation of the temperature at the alveoli can be estimated by processing a temperature signal recorded at the Y-connector $T_y$ and time constant ($\tau$), that depends on flow rate, at the sampling time $\delta$. The discrete time index k is defined such as k=0 is at the end time of a dead volume retrieved from the lungs ($t_{ret}$), and k=N is at the end of the expiratory cycle ($t_d$). The end time of the dead space volume retrieved from the lungs ($t_{ret}$) is determine by integrating the flow ($\dot{V}$) in order to obtain the expired volume versus time $V(t)$ and finding the times ($t_{ret}$) when $V(t)$ becomes greater than the thermal dead volume ($V_{dt}$). The end of the expiratory cycle ($t_d$) is determine as the flow ($\dot{V}$) reverses. Hence, the temperature at the alveoli can be estimated with the equation 8.

$$\hat{T}_L[k]=T_y[k]+f(\dot{V}[k],\dot{V}[k-1],\ldots \dot{V}[k-N],T_y[k],T_y[k-1],\ldots T_y[k-N]) \quad (8)$$

where $f$ is a function of the temperature $T_y$ and flow ($\dot{V}$) measured from the time $t_{ret}$ (discrete time k=0) to the time $t_d$ (discrete time k=N).

Figure 13:
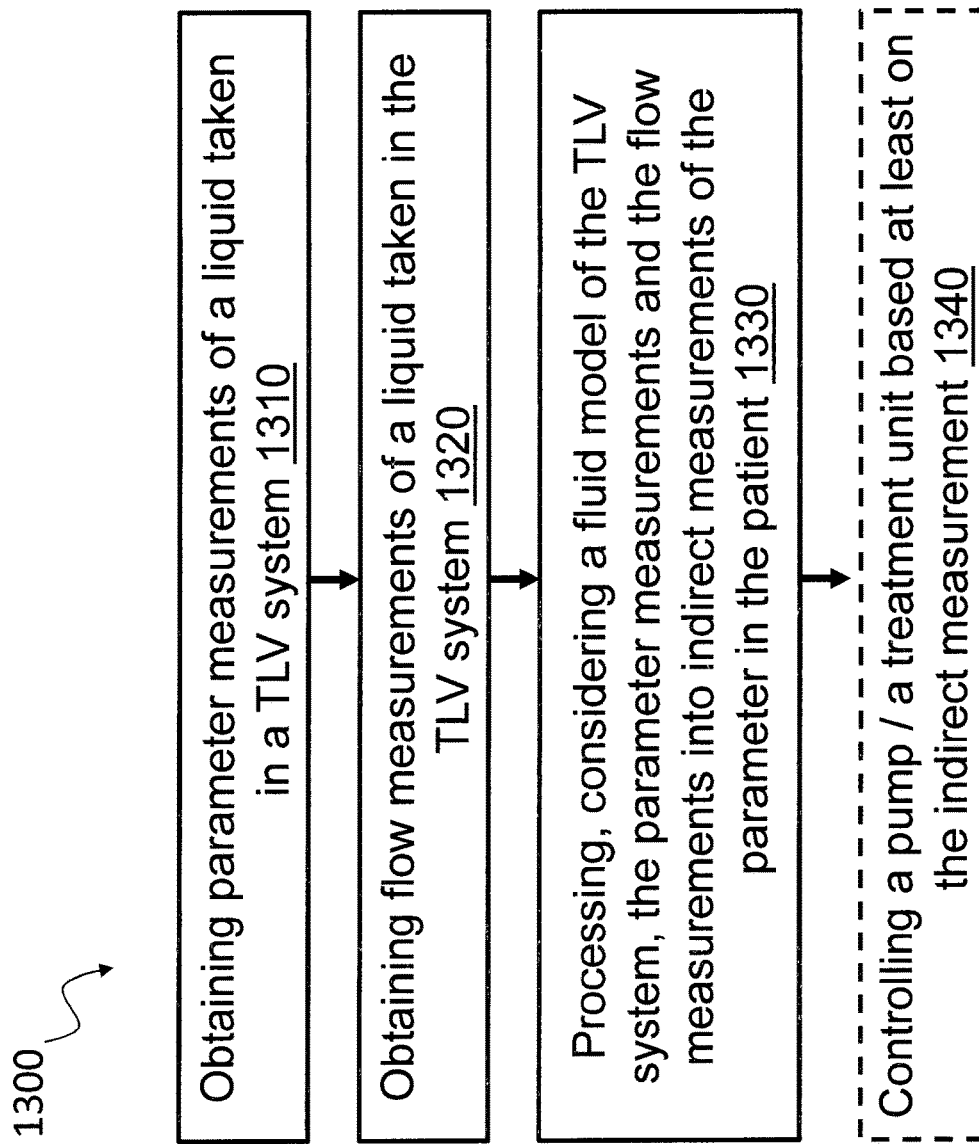
FIG. 13 is a flow chart of an exemplary method for indirect parameter measurement in a total liquid ventilation system according to an embodiment of the present invention.

FIG. 13 shows a flow chart of an exemplary method 1300 for determining an indirect measurement of a parameter in a patient with a total liquid ventilation (TLV) system. The method comprises a) obtaining at least one parameter measurement of a liquid taken in the TLV system comprising a tube having a distal end inserted in a patient's respiratory tract (e.g., an endotracheal tube inserted in a patient's trachea) 1310, b) obtaining at least one flow measurement of a liquid taken in the TLV system 1320 and c) processing, considering a fluid model of the TLV system, the at least one parameter measurement and the least one flow measurement into the indirect measurement of the parameter in the patient 1330.

Optionally, obtaining 1310 the at least one parameter measurement may comprise obtaining at least one pressure measurement of the liquid taken in the TLV and processing 1330 the at least one measurement and the least one flow measurement into the indirect measurement of the parameter in the lung may then further comprise processing the at least one pressure measurement into a pressure drop value within the TLV system considering the fluid model of the TLV system and processing the at least one pressure measurement and the pressure drop value into the indirect measurement of the parameter in the patient's lung.

Steps 1310, 1320 and 1330 may be repeated periodically and/or may be performed in real-time.

Optionally, obtaining 1310 at least one measurement may be performed by receiving data in a plurality of data packets over a network interface.

The method may further comprise (not shown) periodically storing at least the indirect airway pressure value and optionally the pressure measurement, the flow measurement and the pressure drop value into memory.

The method may further comprise (not shown) obtaining a variation of the flow of the liquid. Processing the flow measurement into a pressure drop value within the endotracheal tube may then be performed further considering the variation of the flow of the liquid. Obtaining the variation of the flow of the liquid may also be performed by receiving data in a plurality of data packets over a network interface.

The method may also further comprise (not shown) reading the fluid model of the TLV system from memory.

The method may also optionally further comprise (not shown) determining and/or updating the fluid model of TLV system by determining a resistance of the endotracheal tube and an inertance of the liquid in the endotracheal tube.

The method may also further comprise controlling 1340 a pump of the TLV system based at least on the indirect airway pressure value.

Optionally, obtaining 1310 the at least one parameter measurement may comprise obtaining at least one temperature measurement of a liquid expelled from the lung via the tube. The fluid model of the TLV system may then be a thermodynamic model of the TLV system to estimate the thermal time constant in the TLV system based on flow value. Obtaining the temperature measurement of the liquid may be performed following a pause after an expiratory cycle of the patient.

Processing 1330 the at least one parameter measurement and the least one flow measurement into the indirect measurement of the parameter in the patient may further comprise processing more than one of the at least one flow measurement into flow rate integration to determine a time delay caused by thermal dead volume and processing the at least one temperature measurement considering the time delay the thermal time constant from the TLV model based on the at least one flow measurement.

The indirect measurement of the parameter in the patient may indicate temperature of the patient's lung, of the patient's blood and/or of another of the patient's organ. The temperature of the liquid may be measured at a junction of the tube (e.g., endotracheal) to expiratory and inspiratory circuits of the TLV system.

The method may further comprise controlling 1340 a treatment unit of the TLV system based at least on the indirect temperature measurement.

Those of ordinary skill in the art will realize that the description of the methods, connector and TLV systems for pressure and temperature measurements are illustrative only and are not intended to be in any way limiting. Other embodiments will readily suggest themselves to such persons with ordinary skill in the art having the benefit of the present disclosure. Furthermore, the disclosed methods, connector and TLV systems may be customized to offer valuable solutions to existing needs and problems of related to the lack of maturity of current TLV technology.

In the interest of clarity, not all of the routine features of the implementations of methods, connector and TLV systems are shown and described. It will, of course, be appreciated that in the development of any such actual implementation of the methods, connector and TLV systems, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of artificial ventilators having the benefit of the present disclosure.

Various network links may be implicitly or explicitly used in the context of the present invention. While a link may be depicted as a wireless link, it could also be embodied as a wired link using a coaxial cable, an optical fiber, a category 5 cable, and the like. A wired or wireless access point (not shown) may be present on the link between. Likewise, any number of routers (not shown) may be present and part of the link, which may further pass through the Internet.

The present invention is not affected by the way the different modules exchange information between them. For instance, the memory module and the processor module could be connected by a parallel bus, but could also be connected by a serial connection or involve an intermediate module (not shown) without affecting the teachings of the present invention.

A method is generally conceived to be a self-consistent sequence of steps leading to a desired result. These steps require physical manipulations of physical quantities. Usually, though not necessarily, these quantities take the form of electrical or magnetic/electromagnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities. The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses.

What is claimed is:

1. A method for determining an indirect measurement of a parameter in a patient with a total liquid ventilation (TLV) system, the TLV system comprising a tube having a distal end adapted to be inserted in a respiratory tract of the patient, the method comprising:
    a) obtaining at least one parameter measurement of a liquid taken in the TLV system from at least one first sensor
    b) obtaining at least one flow measurement of the liquid taken in the TLV system from a second sensor;
    c) determining a fluid model of the TLV system based at least in part on one or both of the at least one parameter measurement of the liquid and the at least one flow measurement of the liquid; and
    d) determining the indirect measurement of the parameter in the patient by processing, considering the fluid model of the TLV system, the at least one parameter measurement and the at least one flow measurement,
wherein the indirect measurement of the parameter in the patient is an indirect airway pressure value, the at least one first sensor includes a pressure sensor and the at least one parameter measurement of the liquid taken in the TLV system includes at least one pressure measurement, and wherein processing the at least one parameter measurement and the at least one flow measurement to determine the indirect measurement of the at least one parameter in the patient comprises:
    processing the at least one flow measurement to estimate a pressure drop value within the TLV system considering the fluid model of the TLV system, determining the indirect airway pressure value in the patient by processing the at least one pressure measurement and the pressure drop value, and controlling a pump of the TLV system based at least on the indirect airway pressure value.

2. The method of claim 1 further comprising repeating steps a) to d) periodically.

3. The method of claim 1 further comprising repeating steps a) to d) in real-time.

4. The method of claim 1 wherein obtaining the at least one parameter measurement is performed by receiving data in a plurality of data packets from the at least one first sensor over a network interface.

5. The method of claim 1 further comprising periodically storing at least the indirect airway pressure value.

6. The method of claim 1 further comprising obtaining a variation of a flow of the liquid, wherein processing the at least one flow measurement to estimate the pressure drop value within the TLV system is performed further considering the variation of the flow of the liquid.

7. The method of claim 6 wherein obtaining the variation of the flow of the liquid is performed by receiving data in a plurality of data packets from the second sensor over a network interface.

8. The method of any one of claims 1 and 5 to 7, further comprising reading the fluid model of the TLV system from memory.

9. The method of any one of claims 1 and 5 to 7, further comprising determining and/or updating the fluid model of TLV system by determining a resistance of the tube and an inertance of the liquid in the tube.

10. The method of any one of claims 1 and 5 to 7, wherein the at least one first sensor includes a temperature sensor, wherein obtaining the at least one parameter measurement comprises obtaining at least one temperature measurement from the temperature sensor of a liquid expelled from the patient's respiratory tract via the tube, and wherein the fluid model of the TLV system is a thermodynamic model of the TLV system to estimate a thermal time constant in the TLV system based on the at least one flow measurement.

11. The method of claim 10, wherein obtaining the at least one temperature measurement of the liquid is performed following a pause after an expiratory cycle of the patient.

12. The method of claim 10, wherein processing the at least one parameter measurement and the at least one flow measurement to determine the indirect measurement of the parameter in the patient comprises:

processing at least two flow measurements into a flow rate integration to determine a time delay caused by thermal dead volume;

processing the at least one temperature measurement considering the thermal time constant estimated from the thermodynamic model of the TLV system based on the at least one flow measurement, determining the thermal dead volume, and integrating expiratory flow until the exhaled volume becomes greater than the thermal dead volume, where the resulting integration period is considered as the time delay caused by the thermal dead volume.

13. The method of claim 10, wherein the indirect measurement of the parameter in the patient is an indirect temperature measurement that indicates a temperature of the patient's lung, of the patient's blood and/or of another of the patient's organ.

14. The method of claim 10, wherein the at least one temperature measurement of the liquid is measured at a junction of the tube to expiratory and inspiratory circuits of the TLV system.

15. The method of claim 13, further comprising controlling a treatment unit of the TLV system based at least on the indirect temperature measurement.

16. An analyzer for determining an indirect measurement of a parameter in a patient with a total liquid ventilation (TLV) system, the TLV system comprising a tube having a distal end adapted to be inserted in a patient's respiratory tract, the analyzer comprising:

an interface configured to:
 a) obtain at least one parameter measurement of a liquid taken in the TLV system from at least one first sensor; and
 b) obtain at least one flow measurement of the liquid taken in the TLV system from a second sensor; and a processor configured to:
 c) determine a fluid model of the TLV system based at least in part on one or both of the at least one parameter measurement of the liquid and the at least one flow measurement of the liquid; and
 d) determine the indirect measurement of the parameter in the patient by processing, considering the fluid model of the TLV system, the at least one parameter measurement and the at least one flow measurement, wherein the indirect measurement of the parameter in the patient is an indirect airway pressure value, the at least one first sensor includes a pressure sensor and the at least one parameter measurement of the liquid in the TLV system includes at least one pressure measurement, and wherein the processor when processing the at least one parameter measurement and the at least one flow measurement to determine the indirect measurement of the parameter in the patient, is further configured to:

process the at least one flow measurement to estimate a pressure drop value within the TLV system considering the fluid model of the TLV system, determine the indirect airway pressure value in the patient by processing the at least one pressure measurement and the pressure drop value, and control a pump of the TLV system based at least on the indirect airway pressure value.

17. The analyzer of claim 16, wherein a), b), c), and d) are periodically repeated.

18. The analyzer of claim 16, wherein a), b), c), and d) are performed in real-time.

19. The analyzer of claim 16, wherein the interface is a network interface, and obtaining the at least one parameter measurement from the at least one first sensor further comprising receiving data in a plurality of data packets thereover.

20. The analyzer of claim 16, further comprising a memory module for periodically storing at least the indirect airway pressure value.

21. The analyzer of claim 16, wherein the interface is further configured to obtain a variation of a flow of the liquid, wherein the processor is further configured to process the at least one flow measurement to estimate the pressure drop value within the TLV system considering the variation of the flow of the liquid.

22. The analyzer of claim 21, wherein the interface is a network interface, and obtaining the variation of the flow of the liquid further comprising receiving data from the second sensor in a plurality of data packets thereover.

23. The analyzer of claim 16, further comprising a table stored in a memory module, the table comprising the fluid model of the TLV system.

24. The analyzer of claim 16, wherein the processor is further configured to determine and/or update the fluid model of TLV system by determining a resistance of the tube and an inertance of the liquid in the tube.

25. The analyzer of claim 16, wherein the at least one first sensor includes a temperature sensor, and the interface obtains the at least one parameter measurement by:
obtaining at least one temperature measurement from the temperature sensor of a liquid expelled from the patient's respiratory tract via the tube, and wherein the fluid model of the TLV system is a thermodynamic model of the TLV system to estimate a thermal time constant in the TLV system based on the at least one flow measurement.

26. The analyzer of claim 16, wherein the interface obtains the at least one temperature measurement of the liquid following a pause after an expiratory cycle of the patient.

27. The analyzer of claim 16 or claim 25, wherein the processor, when processing the at least one parameter measurement and the at least one flow measurement to determine the indirect measurement of the parameter in the patient, is further configured to:
process at least two flow measurements into a flow rate integration to determine a time delay caused by thermal dead volume;
process the at least one temperature measurement considering the thermal time constant estimated from the thermodynamic model of the TLV system based on the at least one flow measurement;
determining the thermal dead volume, and
integrating expiratory flow until the exhaled volume becomes greater than the thermal dead volume, where the resulting integration period is considered as the time delay caused by the thermal dead volume.

28. The analyzer of claim 16 or claim 25, wherein the indirect measurement of the parameter in the patient is an indirect temperature measurement that indicates a temperature of the patient's lung, of the patient's blood and/or of another of the patient's organ.

29. The analyzer of claim 16 or claim 25, wherein the at least one temperature measurement of the liquid is measured at a junction of the tube to expiratory and inspiratory circuits of the TLV system.

30. The analyzer of claim 27, wherein the processor is further configured to control a treatment unit of the TLV system based at least on the indirect temperature measurement.

31. A method for determining an indirect measurement of a temperature parameter and an indirect measurement of a pressure parameter in a patient with a total liquid ventilation (TLV) system, the TLV system comprising a tube having a distal end adapted to be inserted in a patient's respiratory tract, the method comprising:
a) obtaining at least one pressure parameter measurement of a liquid taken in the TLV system from a pressure sensor and at least one temperature parameter measurement of the liquid taken in the TLV system from a temperature sensor;
b) obtaining at least one flow measurement of the liquid taken in the TLV system from a flow meter;
c) determining at least one fluid model of the TLV system based at least in part on one or more of the at least one pressure parameter measurement, the at least one temperature parameter measurement, and the at least one flow measurement of the liquid;
d) determining the indirect measurement of the temperature parameter and the indirect measurement of the pressure parameter in the patient by processing, considering the at least one fluid model of the TLV system, the at least one pressure parameter measurement, the at least one temperature parameter measurement, and the at least one flow measurement; and
e) controlling a pump of the TLV system based at least on the indirect measurement of the pressure parameter, wherein the indirect measurement of the pressure parameter corresponds to an indirect airway pressure value.

32. The method of claim 31, further comprising controlling a treatment unit of the TLV system based at least on the indirect measurement of the temperature parameter.

33. An analyzer for determining an indirect measurement of a temperature parameter and an indirect measurement of a pressure parameter in a patient with a total liquid ventilation (TLV) system, the TLV system comprising a tube having a distal end adapted to be inserted in a patient's respiratory tract, the analyzer comprising:
an interface configured to:
a) obtain at least one pressure parameter measurement of a liquid taken in the TLV system from a pressure sensor and at least one temperature parameter measurement of the liquid taken in the TLV system from a temperature sensor; and
b) obtain at least one flow measurement of the liquid taken in the TLV system from a flow meter; and
a processor configured to:
c) determine at least one fluid model of the TLV system based at least in part on one or more of the at least one pressure parameter measurement, the at least one temperature parameter measurement, and the at least one flow measurement of the liquid;
d) determine the indirect measurement of the temperature parameter and the indirect measurement of the pressure parameter by processing, considering the at least one fluid model of the TLV system, the at least one pressure parameter measurement, the at least one temperature parameter measurement, and the at least one flow measurement; and
e) control a pump of the TLV system based at least on the indirect pressure measurement of the pressure parameter, wherein the indirect measurement of the pressure parameter corresponds to an indirect airway pressure value.

34. The analyzer of claim 33, wherein the processor is further configured to control a treatment unit of the TLV system based at least on the indirect measurement of the temperature parameter.

* * * * *